US011490802B2

(12) United States Patent
Hirose et al.

(10) Patent No.: US 11,490,802 B2
(45) Date of Patent: Nov. 8, 2022

(54) OPHTHALMOLOGIC APPARATUS AND METHOD FOR CONTROLLING THE SAME

(71) Applicant: TOPCON CORPORATION, Tokyo (JP)

(72) Inventors: Ryoichi Hirose, Itabashi-ku (JP); Tatsuo Yamaguchi, Warabi (JP)

(73) Assignee: TOPCON CORPORATION, Tokyo (JP)

( * ) Notice: Subject to any disclaimer, the term of this patent is extended or adjusted under 35 U.S.C. 154(b) by 450 days.

(21) Appl. No.: 16/716,508

(22) Filed: Dec. 17, 2019

(65) Prior Publication Data

US 2020/0205653 A1 Jul. 2, 2020

(30) Foreign Application Priority Data

Dec. 26, 2018 (JP) .............................. JP2018-243025

(51) Int. Cl.
*A61B 3/00* (2006.01)
*A61B 3/10* (2006.01)

(52) U.S. Cl.
CPC ............ *A61B 3/0025* (2013.01); *A61B 3/102* (2013.01)

(58) Field of Classification Search
CPC ............ A61F 2009/00872; A61F 9/008; A61F 2009/0088; A61F 9/00829; A61F 9/00806;

(Continued)

(56) References Cited

U.S. PATENT DOCUMENTS

2010/0123774 A1* 5/2010 Tomita ................. H04N 13/327
348/54
2015/0216408 A1 8/2015 Brown et al.
(Continued)

FOREIGN PATENT DOCUMENTS

EP 3 384 826 A2 10/2018
JP 2012-147977 A 8/2012
(Continued)

OTHER PUBLICATIONS

Extended European Search Report dated Apr. 28, 2020, issued in corresponding European Patent Application No. 19213745.3.
(Continued)

*Primary Examiner* — Brandi N Thomas
(74) *Attorney, Agent, or Firm* — Xsensus LLP

(57) ABSTRACT

An ophthalmologic apparatus includes a data acquisition unit, a storage unit, and a correction unit. The data acquisition unit includes a concave mirror and an optical scanner configured to deflect light from a light source to guide to a reflective surface of the concave mirror. The data acquisition unit is configured to acquire a first data set group in an A-scan direction by performing optical coherence tomography on a subject's eye placed at a subject's eye position or a conjugate position of the subject's eye position using light reflected by the reflective surface. The storage unit is configured to store correction data for correcting an incident angle of the light at the subject's eye position depending on a deflection angle of the light by the optical scanner. The correction unit is configured to generate a second data set group by correcting at least a part of the first data set group based on the correction data stored in the storage unit.

17 Claims, 13 Drawing Sheets

(58) Field of Classification Search
CPC .. A61F 2009/00882; A61F 2009/00897; A61F 9/00804; A61F 9/00808; A61F 9/00827; A61F 9/00836; A61F 9/00838; A61F 2009/00844; A61F 2009/00846; A61F 9/00; A61F 9/007; A61F 9/009; A61F 2009/00848; A61F 9/00812; A61F 9/00814; G06T 2207/10016; G06T 5/005; G06T 15/20; G06T 2207/10024; G06T 5/00; G06T 5/002; G06T 5/006; G06T 19/006; G06T 1/00; G06T 2207/30041; G06T 5/20; G06T 15/04; G06T 2207/10101; G06T 5/003; G06T 5/50; G06T 7/00; G06T 7/73; G06T 1/0007; G06T 2207/10012; G06T 2207/10052; G06T 2207/20192; G06T 3/20; G06T 3/40; G06T 3/60; G06T 7/13; G06T 11/006; G06T 15/005; G06T 2207/20012; G06T 3/0056; G06T 1/20; G06T 11/40; G06T 15/30; G06T 15/40; G06T 15/405; G06T 15/50; G06T 15/83; G06T 19/20; G06T 2200/24; G06T 2207/20032; G06T 3/4015; G06T 3/403; G06T 7/0002; G06T 7/0014; G06T 11/00; G06T 11/206; G06T 15/00; G06T 15/10; G06T 15/87; G06T 17/00; G06T 17/10; G06T 19/00; G06T 2207/10056; G06T 2207/20036; G06T 2207/20081; G06T 2207/20084; G06T 2210/41; G06T 2219/2004; G06T 2219/2016; G06T 3/0006; G06T 3/4007; G06T 7/0016; G06T 7/194; G06T 7/20; G06T 7/223; G06T 7/231; G06T 7/254; G06T 7/30; G06T 7/33; G06T 7/37; G06T 7/50; G06T 7/593; G06T 7/97; G06T 1/0064; G06T 11/001; G06T 11/003; G06T 13/20; G06T 15/02; G06T 15/06; G06T 15/08; G06T 17/20; G06T 19/003; G06T 2200/04; G06T 2200/32; G06T 2207/10004; G06T 2207/10068; G06T 2207/10141; G06T 2207/20021; G06T 2207/20056; G06T 2207/20064; G06T 2207/20132; G06T 2207/20204; G06T 2207/20221; G06T 2207/30036; G06T 2207/30144; G06T 2207/30148; G06T 2207/30196; G06T 2207/30201; G06T 2207/30204; G06T 2207/30216; G06T 2207/30232; G06T 2207/30244; G06T 2210/44; G06T 3/0018; G06T 3/0068; G06T 3/0093; G06T 3/4038; G06T 5/007; G06T 5/009; G06T 5/40; G06T 7/0004; G06T 7/001; G06T 7/0012; G06T 7/11; G06T 7/12; G06T 7/149; G06T 7/168; G06T 7/215; G06T 7/248; G06T 7/262; G06T 7/32; G06T 7/337; G06T 7/251; G06T 7/55; G06T 7/74; G06T 7/80; G06T 7/85; G06T 7/90; G06T 9/00; G06T 9/001

See application file for complete search history.

(56) References Cited

U.S. PATENT DOCUMENTS

| | | | |
|---|---|---|---|
| 2018/0279872 A1 | 10/2018 | Okamoto et al. | |
| 2018/0289260 A1* | 10/2018 | Matsunobu | A61B 3/1225 |

FOREIGN PATENT DOCUMENTS

| | | | | |
|---|---|---|---|---|
| JP | 6677385 | * | 11/2015 | .......... H04N 13/327 |
| JP | 2018-061622 A | | 4/2018 | |
| JP | 2018-167000 A | | 11/2018 | |
| JP | 2019-088382 A | | 6/2019 | |
| JP | 2019-154996 A | | 9/2019 | |
| WO | 2016/103484 A1 | | 6/2016 | |
| WO | 2016/103489 A1 | | 6/2016 | |
| WO | 2018/069346 A1 | | 4/2018 | |
| WO | 2019/203312 A1 | | 10/2019 | |

OTHER PUBLICATIONS

Office Action dated Sep. 13, 2022 in Japanese Patent Application No. 2018-243025, 6 pages.

* cited by examiner

OPHTHALMOLOGIC APPARATUS AND METHOD FOR CONTROLLING THE SAME

CROSS-REFERENCE TO RELATED APPLICATION

This application is based upon and claims the benefit of priority from Japanese Patent Application No. 2018-243025, filed Dec. 26, 2018; the entire contents of which are incorporated herein by reference.

FIELD

The disclosure relates to an ophthalmologic apparatus and a method for controlling the same.

BACKGROUND

In recent years, attention has been drawn to optical coherence tomography (OCT) which is used to measure the morphology of an object to be measured or to image using light beam emitted from a laser light source or the like. Since OCT does not have invasiveness to human body as X-ray CT (Computed Tomography) does, development of application of OCT in medical field and biology field is particularly expected. For example, in the ophthalmologic field, apparatuses for forming images of the fundus or the cornea have been in practical use. Such apparatuses using OCT (OCT apparatuses) can be used to observe a variety of sites (a fundus, or an anterior segment) of a subject's eye. In addition, because of the ability to acquire high precision images, the OCT apparatuses are applied to the diagnosis of various eye diseases.

In a measuring (imaging) using OCT, acquiring a measurement result with a wider angle and higher definition is demanded. For example, ophthalmologic apparatuses using an ellipsoidal mirror are disclosed in Japanese Unexamined Patent Application Publication No. 2018-61622 and Japanese Unexamined Patent Application Publication No. 2018-167000. The ophthalmologic apparatuses disclosed in Japanese Unexamined Patent Application Publication No. 2018-61622 and Japanese Unexamined Patent Application Publication No. 2018-167000 are configured to deflect the measurement light using the optical scanner, to reflect the deflected measurement light using the ellipsoidal mirror, and to guide the reflected measurement light toward the subject's eye.

SUMMARY

One aspect of some embodiments is an ophthalmologic apparatus including: a data acquisition unit including a concave mirror and an optical scanner configured to deflect light from a light source to guide to a reflective surface of the concave mirror, and configured to acquire a first data set group in an A-scan direction by performing optical coherence tomography on a subject's eye placed at a subject's eye position or a conjugate position of the subject's eye position using light reflected by the reflective surface; a storage unit configured to store correction data for correcting an incident angle of the light at the subject's eye position depending on a deflection angle of the light by the optical scanner; and a correction unit configured to generate a second data set group by correcting at least a part of the first data set group based on the correction data stored in the storage unit.

Another aspect of some embodiments is a method of controlling an ophthalmologic apparatus including a concave mirror and an optical scanner configured to deflect light from a light source to guide to a reflective surface of the concave mirror. The method includes: a data acquisition step of acquiring a first data set group in an A-scan direction by performing optical coherence tomography on a subject's eye placed at a subject's eye position or a conjugate position of the subject's eye position using light reflected by the reflective surface; and a correction step of generating a second data set group by correcting at least a part of the first data set group based on correction data for correcting an incident angle of the light at the subject's eye position depending on a deflection angle of the light by the optical scanner.

DETAILED DESCRIPTION

Figure 1:
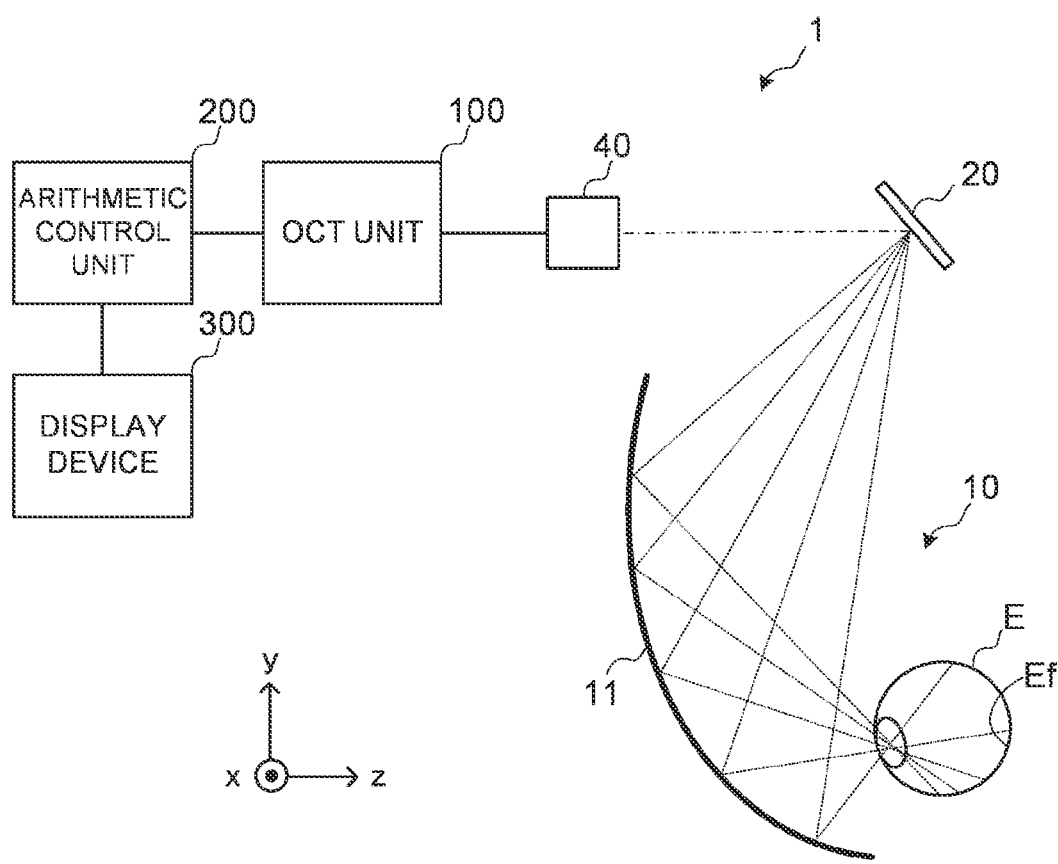
FIG. 1 is a schematic diagram illustrating an example of the configuration of an ophthalmologic apparatus according to embodiments.

In ophthalmologic apparatuses using the ellipsoidal mirror, the deflection angle of the measurement light by the optical scanner and the incident angle of the measurement light at the subject's eye position where the subject's eye is arranged have a non-linear relationship. Therefore, when the optical scanner is linearly deflected and the A-scan is performed at substantially equal time intervals, the intervals of the incident angles of the measurement light at the subject's eye position are non-uniform. That is, even if a simple deflection control is performed on the optical scanner, it is difficult to obtain a highly accurate OCT measurement result at a desired measurement site.

The decrease in the accuracy of the OCT measurement result due to such non-uniform intervals of the incidence angle of the measurement light is not limited to ophthalmologic apparatuses using an ellipsoidal mirror. The same applies to ophthalmologic apparatuses using a concave mirror having a reflecting surface formed in a concave shape (including one having a reflective surface formed as a free-form surface).

According to some embodiments of the present invention, an ophthalmologic apparatus capable of performing OCT measurement with a wider angle and higher accuracy using a concave mirror, and a method of controlling the ophthalmologic apparatus can be provided.

Referring now to the drawings, exemplary embodiments of an ophthalmologic apparatus and a method of controlling the ophthalmologic apparatus according to the present invention are described below. Any of the contents of the documents cited in the present specification and arbitrary known techniques may be applied to the embodiments below.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

An ophthalmologic apparatus according to embodiments includes a concave mirror and an optical scanner. A reflective surface of the concave mirror is formed in a concave shape. The optical scanner deflects measurement light in a predetermined deflection angle range to guide the deflected light to the reflective surface of the concave mirror. The ophthalmologic apparatus can perform optical coherence tomography (OCT) on a subject's eye using the measurement light reflected by the reflective surface. In some embodiments, the ophthalmologic apparatus acquires a data set group in an A-scan direction (first data set group) by performing OCT, and generates a new data set group (second data set group) by correcting at least a part of the data set group based on correction data for correcting an incident angle (interval of the incident angle) of the measurement light at a subject's eye position (or near the subject's eye position), where the subject's eye is placed, depending on a deflection angle of the measurement light by the optical scanner. In some embodiments, the data set group is a data set group of reflection intensity profile data in the A-scan direction obtained by performing Fourier transformation etc. on detection data (detection result) of interference light. In some embodiments, the data set group is a data set group of A-scan image data obtained by imaging the reflection intensity profile. In some embodiments, the data set group is a data set group of the detection data of the interference light.

Thereby, a data set group in the A-scan direction can be acquired in consideration of the change characteristics (deflection operation characteristics) of the deflection angle of the measurement light by the optical scanner and the change characteristics of the incident angle of the measurement light at the subject's eye position due to the shape of the reflective surface of the concave mirror. For example, a data set group at the uniformly arranged scan positions can be generated from the data set group acquired at the unevenly distributed scan positions due to the reflection from the reflective surface of the concave mirror. Further, for example, a data set group based on the measurement light incident on the subject's eye at the subject's eye position at intervals of substantially equal incident angle can be acquired. Further, for example, a data set group acquired at high density only at a desired site can be generated from the data set group acquired at the unevenly distributed scan positions due to the reflection from the reflective surface of the concave mirror.

Hereinafter, in the embodiments, the case of using the swept source type OCT method in the measurement or the imaging (photographing) using OCT will be described. However, the configuration according to the embodiments can also be applied to an ophthalmologic apparatus using other type of OCT (for example, spectral domain type OCT).

Hereinafter, the case in which the optical scanner includes a galvano scanner, performs linear operation in a predetermined deflection angle range, and performs non-linear operation in another deflection angle range will be described. However, the following embodiments can also be applied when the optical scanner performs linear operation over the entire range of the predetermined deflection angle range. Further, the following embodiments can also be applied when the optical scanner includes a deflection element (for example, a resonant mirror, a polygon mirror, etc.) other than the galvano scanner.

Further, hereinafter, a deflection angle versus time characteristics will be described as an example of the operating characteristics of the optical scanner. However, the following embodiments can be applied to other operating characteristics of the optical scanner.

Further, hereinafter, the case in which the data set group of the A-scan image data is corrected. However, the following embodiments can be applied when the data set group of the reflection intensity profile data etc. is corrected.

In this specification, images acquired using OCT may be collectively referred to as "OCT images". Also, the measurement operation for forming OCT images may be referred to as OCT measurement.

The ophthalmologic apparatus according to some embodiments includes any one or more of an ophthalmologic imaging apparatus, an ophthalmologic measuring apparatus, and an ophthalmologic therapy apparatus. The ophthalmologic imaging apparatus included in the ophthalmologic apparatus according to some embodiments includes, for example, any one or more of a fundus camera, a scanning laser ophthalmoscope, a slit lamp ophthalmoscope, a surgical microscope, and the like. Further, the ophthalmologic measuring apparatus included in the ophthalmologic apparatus according to some embodiments includes any one or more of an eye refractivity examination apparatus, a tonometer, a specular microscope, a wave-front analyzer, a perimeter, a microperimeter, and the like, for example. Further, the ophthalmologic therapy apparatus included in the ophthalmologic apparatus according to some embodiments includes any one or more of a laser therapy apparatus, a surgical apparatus, a surgical microscope, and the like, for example.

The ophthalmologic apparatus according to the following embodiments includes an OCT apparatus capable of performing OCT measurement. Hereinafter, an ophthalmologic apparatus capable of performing OCT measurement on a fundus of the subject's eye will be described as an example. However, the ophthalmologic apparatus according to the embodiments may be capable of performing OCT measurement on an anterior segment of the subject's eye. In some embodiments, a measurement site of the OCT measurement and/or a range of the OCT measurement are changed by moving a lens for changing focal position of the measurement light. In some embodiments, the ophthalmologic apparatus has a configuration capable of performing OCT measurement on the fundus, OCT measurement on the anterior segment, and OCT measurement on the whole eyeball including the fundus and anterior segment, by adding one or more attachments (objective lens, front lens, etc.). In some embodiments, in the ophthalmologic apparatus for measuring fundus, OCT measurement is performed on the anterior segment, by making the measurement light incident on the subject's eye, the measurement light having been converted into a parallel light flux by arranging a front lens between a collimator lens unit (described later) or an optical scanner and the subject's eye.

<Configuration>

FIG. 1 illustrates an example of the configuration of the ophthalmologic apparatus according to the embodiments.

The ophthalmologic apparatus 1 according to the embodiments includes an optical system 10, a collimator lens unit 40, an OCT unit 100, an arithmetic control unit 200, and a display device 300. In some embodiments, the OCT unit 100 includes the collimator lens unit 40. In some embodiments, the optical system 10 includes the collimator lens unit 40 and the OCT unit 100.

The optical system 10 includes an ellipsoidal mirror 11 and an optical scanner 20. A reflective surface of the ellipsoidal mirror 11 is an elliptical surface. The ellipsoidal mirror 11 is an example of the concave mirror. In some embodiments, the optical system 10 includes a concave mirror whose reflective surface is formed in a concave shape, instead of the ellipsoidal mirror 11. In some embodiments, the reflective surface of the concave mirror is formed to be a free-form surface.

The ellipsoidal mirror 11 has two optically conjugate focal points (first focal point, second focal point). The optical scanner 20 (deflected surface of the optical scanner 20) is disposed at the first focal point of the ellipsoidal mirror 11, near the first focal point, a position optically conjugate with the first focal point (conjugate position of the first focal point), or near the position optically conjugate with the first focal point. The subject's eye position, where the subject's eye E (pupil) is arranged, is disposed at the second focal point of the ellipsoidal mirror 11, near the second focal point, a position optically conjugate with the second focal point (conjugate position of the second focal point), or near the position optically conjugate with the second focal point.

The optical scanner 20 is disposed at a position optically conjugate with the pupil of the subject's eye E or near the position. The optical scanner 20 deflects measurement light (measurement light traveling along the optical path for OCT) emitted from the collimator lens unit 40 in a predetermined deflection angle range. The optical scanner 20 can deflect the measurement light in a one-dimensionally or two-dimensional manner.

In case that the optical scanner 20 deflects the measurement light in a one-dimensionally manner, the optical scanner 20 includes a galvano scanner capable of deflecting the measurement light in a predetermined deflection direction within a predetermined deflection angle range. In case that the optical scanner 20 deflects the measurement light in a two-dimensionally manner, the optical scanner 20 includes a first galvano scanner and a second galvano scanner. The first galvano scanner deflects the measurement light so as to scan a photographing (imaging) site (fundus Ef or the anterior segment) in a horizontal direction orthogonal to the optical path (optical axis) of the measurement light. The second galvano scanner deflects the measurement light deflected by the first galvano mirror so as to scan the photographing site in a vertical direction orthogonal to the optical path (optical axis) of the measurement light. Examples of scan mode with the measurement light performed by the optical scanner 20 include horizontal scan, vertical scan, cross scan, radial scan, circle scan, concentric scan, helical (spiral) scan, and the like.

The collimator lens unit 40 includes a collimator lens. The collimator lens is disposed on an optical axis of an interference optical system included in the OCT unit 100. The collimator lens converts a light flux of the measurement light emitted from the end of an optical fiber into a parallel light flux. The optical fiber is connected to the OCT unit 100 and guides the measurement light to the end. The end of this optical fiber is, for example, located at a position optically conjugate with the fundus Ef of the subject's eye E or near the position.

In addition to the configuration illustrated in FIG. 1, the optical system 10 may be provided with an optical system (observation optical system, imaging optical system, etc.) for photographing the subject's eye E (fundus Ef or the anterior segment) from the front, and/or an alignment optical system.

Further, the optical system 10 may have a configuration for providing a function associated with the inspection. For example, the optical system 10 may include a fixation optical system for projecting a visual target (fixation target) for fixating the subject's eye E onto the fundus Ef of the subject's eye E. The optical system 10 may also be provided with a configuration for focusing of the interference optical system included in the OCT unit 100 and the like. The optical system 10 may be further provided with a light source (anterior segment illumination light source) for illuminating the anterior segment of the subject's eye E.

As described later, the OCT unit 100 is provided with a part of an optical system (interference optical system) and a mechanism which are used for performing OCT.

The arithmetic control unit 200 controls each part of the ophthalmologic apparatus 1. The arithmetic control unit 200 includes one or more processors and executes various types of arithmetic operations and controls by executing processes corresponding to programs stored in advance.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

The display device 300 displays various information. The display device 300 includes a display device such as a liquid crystal display. The display device 300 displays the above information under the control of the arithmetic control unit 200. Examples of the information displayed on the display device 300 include information corresponding to the control result by the arithmetic control unit 200, information (image) corresponding to the calculation result by the arithmetic control unit 200, and information (image) acquired by an optical system (not shown).

In addition to these elements, an arbitrary element or a unit, such as a member (chin rest, forehead pad, etc.) for supporting a face of the subject, a lens unit (for example, an attachment for an anterior segment OCT) for switching the target site of OCT, and the like, may be provided in the ophthalmologic apparatus 1. In some embodiments, the lens unit is configured to be manually inserted and removed between the subject's eye E and an objective lens (not shown). In some embodiments, the lens unit is configured to be automatically inserted and removed between the subject's eye E and the objective lens, under the control of the controller 210 described later.

[OCT Unit 100]

Figure 2:
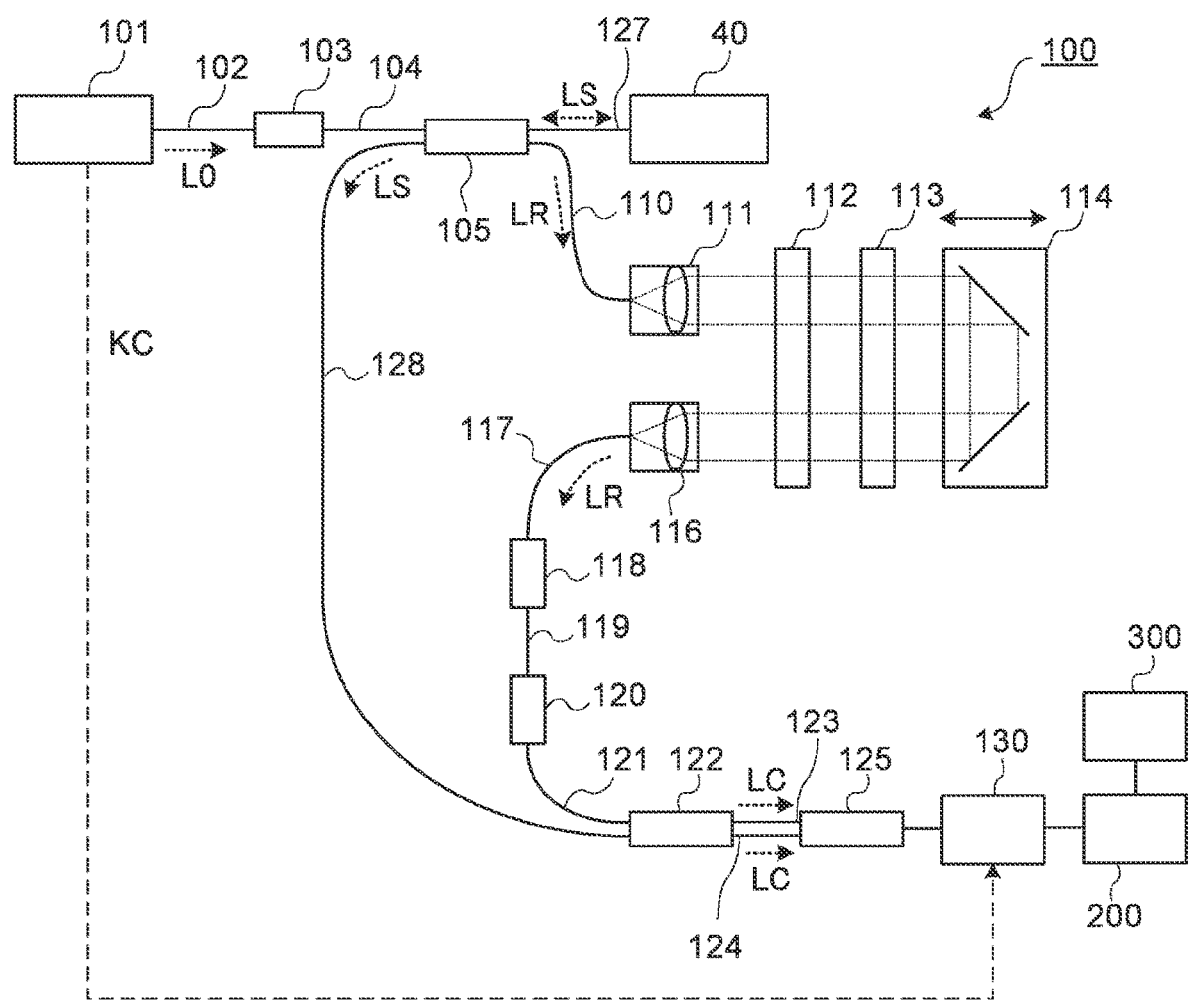
FIG. 2 is a schematic diagram illustrating an example of the configuration of an ophthalmologic apparatus according to the embodiments.

An example of the configuration of the OCT unit 100 is shown in FIG. 2. The OCT unit 100 is provided with an optical system for acquiring OCT images of the subject's eye E. The optical system includes an interference optical system that splits light from a wavelength sweeping type (i.e., a wavelength scanning type) light source into measurement light and reference light, makes the measurement light returning from the subject's eye E and the reference light having traveled through the reference optical path interfere with each other to generate interference light, and detects the interference light. The detection result of the interference light obtained by the interference optical system (i.e., the detection signal) is an interference signal indicating the spectrum of the interference light, and is sent to the arithmetic control unit 200.

Like swept source type ophthalmologic apparatuses commonly used, the light source unit 101 includes a wavelength sweeping type (i.e., a wavelength scanning type) light source capable of sweeping (scanning) the wavelengths of emitted light. The wavelength sweeping type light source includes a laser light source that includes a resonator. The light source unit 101 temporally changes the output wavelengths within the near-infrared wavelength bands that cannot be visually recognized with human eyes.

The light L0 output from the light source unit 101 is guided to the polarization controller 103 by the optical fiber 102, and the polarization state of the light L0 is adjusted. The polarization controller 103, for example, applies external stress to the looped optical fiber 102 to thereby adjust the polarization state of the light L0 guided through the optical fiber 102.

The light L0 whose polarization state has been adjusted by the polarization controller 103 is guided to the fiber coupler 105 through the optical fiber 104, and is split into the measurement light LS and the reference light LR.

The reference light LR is guided to the collimator 111 through the optical fiber 110. The reference light LR is converted into a parallel light beam by the collimator 111. Then, the reference light LR is guided to the optical path length changing unit 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS.

The optical path length changing unit 114 is movable in directions indicated by the arrow in FIG. 2, thereby changing the length of the optical path of the reference light LR. Through such movement, the length of the optical path of the reference light LR is changed. The change in the optical path length is used for the correction of the optical path length according to the axial length of the subject's eye E, for the adjustment of the interference state, or the like. The optical path length changing unit 114 includes, for example, a corner cube and a movement mechanism for moving the corner cube. In this case, the corner cube in the optical path length changing unit 114 changes the traveling direction of the reference light LR that has been made into the parallel light flux by the collimator 111 in the opposite direction. The optical path of the reference light LR incident on the corner cube and the optical path of the reference light LR emitted from the corner cube are parallel.

The reference light LR that has traveled through the optical path length changing unit 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through the optical fiber 127, and is made into the parallel light beam by the collimator lens unit 40. The measurement light LS, which has been made into a parallel light beam, is deflected by the optical scanner 20, and is guided to the reflective surface of the ellipsoidal mirror 11. The measurement light LS is reflected by the reflective surface of the ellipsoidal mirror 11 and enters the eye through the pupil of the subject's eye E at the subject's eye position. The measurement light LS is scattered (and reflected) at various depth positions of the subject's eye E. The returning light of the measurement light LS including such backscattered light advances through the same path as the outward path in the opposite direction and is led to the fiber coupler 105, and then reaches the fiber coupler 122 through the optical fiber 128.

The fiber coupler 122 combines (interferes) the measurement light LS incident through the optical fiber 128 and the reference light LR incident through the optical fiber 121 to generate interference light. The fiber coupler 122 generates a pair of interference light LC by splitting the interference light generated from the measurement light LS and the reference light LR at a predetermined splitting ratio (for example, 1:1). The pair of the interference light LC emitted from the fiber coupler 122 is guided to the detector 125 through the optical fibers 123 and 124, respectively.

The detector 125 is, for example, a balanced photodiode that includes a pair of photodetectors for respectively detecting the pair of interference light LC and outputs the difference between the pair of detection results obtained by the pair of photodetectors. The detector 125 sends the detection result (i.e., interference signal) to the data acquisition system (DAQ) 130. A clock KC is supplied from the light source unit 101 to the DAQ 130. The clock KC is generated in the light source unit 101 in synchronization with the output timing of each wavelength sweeping (scanning) within a predetermined wavelength range performed by the wavelength sweeping type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs the sampling of the detection result obtained by the detector 125 based on the clock KC. The DAQ 130 sends the result of the sampling of the detection result obtained by the detector 125 to the arithmetic control unit 200. For example, the arithmetic control unit 200 performs the Fourier transform etc. on the spectral distribution based on the detection result obtained by the detector 125 for each series of wavelength scanning (i.e., for each A line). With this, the reflection intensity profile for each A line is formed. In addition, the arithmetic control unit 200 forms image data by applying imaging processing to the reflection intensity profiles for the respective A lines.

[Arithmetic Control Unit 200]

The arithmetic control unit 200 analyzes the detection signals fed from the DAQ 130 to form an OCT image. The arithmetic processing for the OCT image formation is performed in the same manner as in the conventional swept-source-type OCT apparatus.

Further, the arithmetic control unit 200 controls each part of the optical scanner 20, the movement mechanism 150, the OCT unit 100, and the display device 300.

Further, as the control of the OCT unit 200, the arithmetic control unit 200 controls: the operation of the light source unit 101; the operation of the optical path length changing unit 114; the operations of the attenuator 120; the operation of the polarization controllers 103 and 118; the operation of the detector 125; the operation of the DAQ 130; and the like.

As the control of the display device 300, the arithmetic control unit 200 causes the display device 300 to display an OCT image of the subject's eye E, information for prompting an examiner or the subject to proceed of OCT measurement, and the like.

As in the conventional computer, the arithmetic control unit 200 includes a processor, RAM, ROM, hard disk drive, and communication interface, for example. A storage device such as the hard disk drive stores a computer program for controlling the ophthalmologic apparatus 1. The arithmetic control unit 200 may include various kinds of circuitry such as a circuit board for forming OCT images. In addition, the arithmetic control unit 200 may include an operation device (or an input device) such as a keyboard and a mouse, and a display device such as an LCD.

[Control System]

Figure 3:
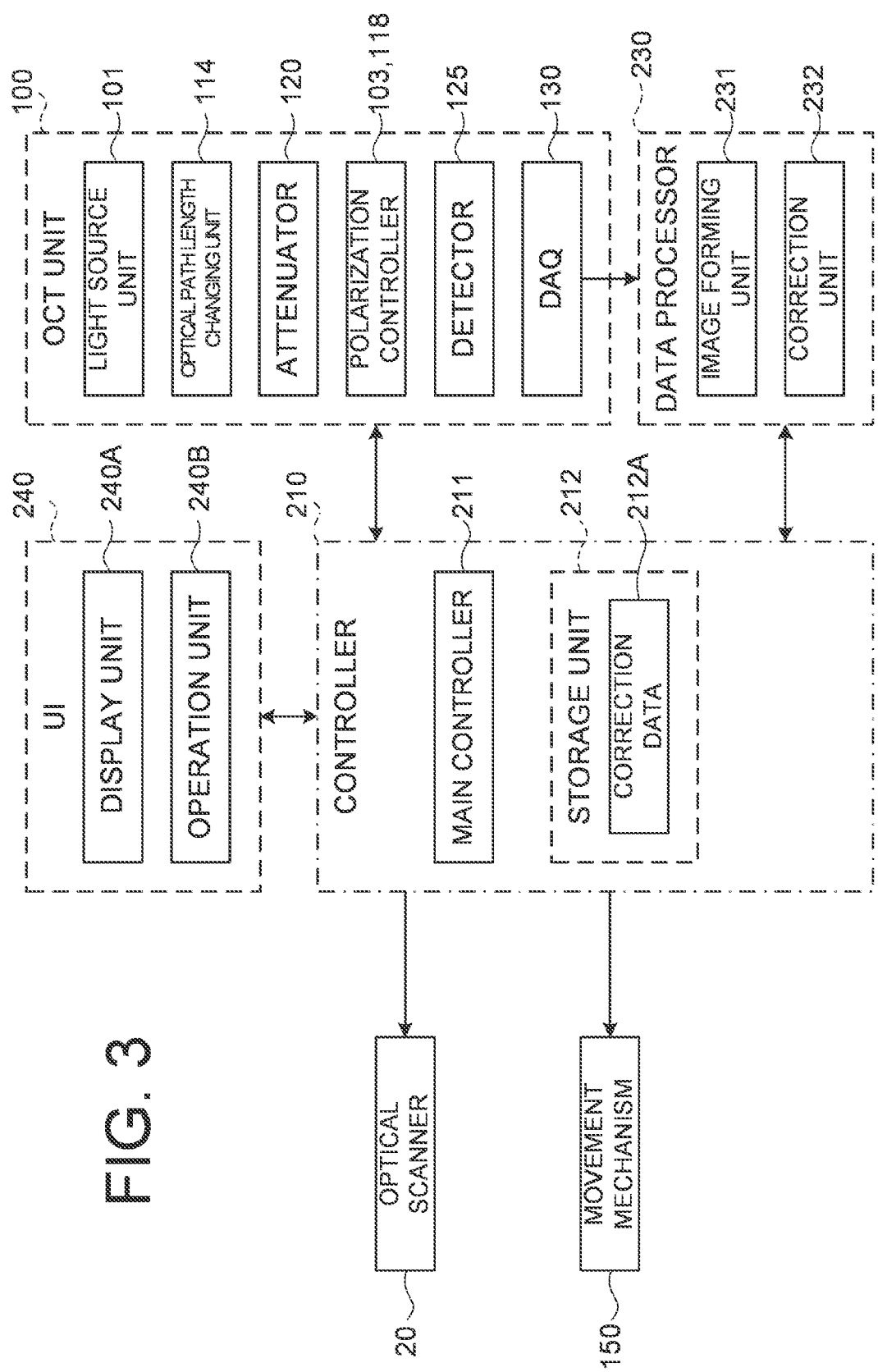
FIG. 3 is a schematic block diagram illustrating an example of the configuration of the ophthalmologic apparatus according to the embodiments.

The arithmetic control unit 200 includes the controller 210 and a data processor 230, as shown in FIG. 3. The functions of the arithmetic control unit 200 are realized by one or more processors. In some embodiments, the functions of the arithmetic control unit 200 are realized by a control processor that realizes the function of the controller 210 and a data processing processor that realizes the function of the data processor 230.

(Controller)

The controller 210 executes various controls. The controller 210 includes a main controller 211 and a storage unit 212.

(Main Controller)

The main controller 211 includes a processor and controls each part of the ophthalmologic apparatus 1. For example, the main controller 211 controls the optical scanner 20, the entire optical system (movement mechanism 150), and the like. Further, the main controller 211 controls components of the OCT unit 100 such as the light source unit 101, the optical path length changing unit 114, the attenuator 120, the polarization controllers 103 and 118, the detector 125, and the DAQ 130.

Further, the main controller 211 can control the fixation optical system (not shown) to present the fixation target to the subject's eye E so as to guide fixation to the fixation position set manually or automatically.

Further, the main controller 211 can control a focusing lens (not shown) to move the focusing lens in the optical axis direction of the interference optical system to change the focus point of the measurement light. For example, the focus position of the measurement light LS can be arranged at the fundus Ef or near the fundus Ef by moving the focusing lens to a first lens position. For example, by moving the focusing lens to a second lens position, the focus position of the measurement light can be arranged at a far point position and the measurement light LS can be made into a parallel light beam. The focus position of the measurement light LS corresponds to the depth position (z position) of the beam waist of the measurement light LS.

The movement mechanism 150 three-dimensionally moves at least a part of the optical system 10 (for example, interference optical system), for example. In a typical example, the movement mechanism 150 includes a mechanism for moving at least the optical system 10 in a x direction (left-right direction, horizontal direction), a mechanism for moving it in a y direction (up-down direction, vertical direction), and a mechanism for moving it in a z direction (depth direction, front-back direction). The mechanism for moving in the x direction includes a x stage movable in the x direction and a x movement mechanism for moving the x stage, for example. The mechanism for moving in the y direction includes a y stage movable in the y direction and a y movement mechanism for moving the y stage, for example. The mechanism for moving in the z direction includes a z stage movable in the z direction and a z movement mechanism for moving the z stage, for example. Each movement mechanism includes an actuator such as a pulse motor, and operates under the control of the main controller 211.

The control for the movement mechanism 150 is used for alignment and tracking. Here, tracking is to move the optical system of the apparatus according to the movement of the subject's eye E. To perform tracking, alignment and focus adjustment are performed in advance. The tracking is a function of maintaining a suitable positional relationship in which alignment and focusing are matched by causing the position of the optical system of the apparatus and the like to follow the eye movement. In some embodiments, the movement mechanism 150 is configured to be controlled to change the optical path length of the reference light (that is, the difference of the optical path length between the optical path of the measurement light and the optical path of the reference light).

In the case of manual alignment, a user operates a user interface (UI) 240 described later to relatively move the optical system and subject's eye E so as to cancel the displacement of the subject's eye E with respect to the optical system. For example, the main controller 211 controls the movement mechanism 150 to relatively move the optical system and the subject's eye E by outputting a control signal corresponding to the operation content with respect to the user interface 240 to the movement mechanism 150.

In the case of automatic alignment, the main controller 211 controls the movement mechanism 150 to relatively move the optical system and the subject's eye E so as to cancel the displacement of the subject's eye E with respect to the optical system. For example, the movement mechanism 150 is controlled so as to cancel a displacement between (a reference position of) the image of the subject's eye E acquired using imaging optical system (not shown) and a reference position of the optical system. In some embodiments, the main controller 211 controls the movement mechanism 150 to relatively move the optical system and the subject's eye E by outputting a control signal to the movement mechanism 150 so that the optical axis of the optical system substantially coincides with the axis of the subject's eye E and the distance of the optical system with respect to the subject's eye E is a predetermined working distance. Here, the working distance is a preset value which is called a working distance of the objective lens (not shown), and it means the distance between the subject's eye E and the optical system when measuring (imaging) using the optical system.

The main controller 211 controls the OCT unit 100 etc. to control the OCT measurement. The main controller 211 is capable of performing a plurality of preliminary operations prior to OCT measurement. The preliminary operations may include alignment, focus adjustment, optical path length difference adjustment, polarization adjustment, and the like. The plurality of preliminary operations is performed in a predetermined order. In some embodiments, the plurality of preliminary operations is performed in an order described above.

It should be noted that the types and the orders of the preliminary operations are not so limited, and they may be optional. For example, the preliminary operations may further include small-pupil judgment. The small-pupil judgment is a preliminary operation to judge whether the pupil of the subject's eye E is small or not (whether the subject's eye E is microcoria or not). The small-pupil judgment may be performed between the rough focus adjustment and the optical path length difference adjustment. In some embodiments, the small-pupil judgment includes, for example, a series of processes as follows: acquiring a front image (anterior segment image) of the subject's eye E; specifying an image region corresponding to the pupil; calculating the size (e.g., diameter, circumference length) of the pupil region; judging whether the pupil of the subject's eye E is small or not based on the calculated size (threshold processing); and controlling a diaphragm (not shown) when judged that the pupil of the subject's eye E is small. In some embodiments, the calculation of the size of the pupil region includes processing of circularly or elliptically approximating the pupil region.

The focus adjustment is performed on the basis of interference sensitivity of OCT measurement, for example. For example, the focus adjustment can be performed by: monitoring interference intensity (interference sensitivity) of interference signal acquired by performing OCT measurement of the subject's eye E; searching the position of the focusing lens so as to maximize the interference intensity; and moving the focusing lens to the searched position.

To perform the optical path length difference adjustment, the optical system is controlled so that a predetermined position on the subject's eye E is a reference position of a measurement range in the depth direction. The control is performed on the optical path length changing unit 114. Thereby, the difference of the optical path length between the measurement optical path and the reference optical path is adjusted. By setting the reference position in the optical path length difference adjustment, OCT measurement can be performed with high accuracy over a desired measurement range in the depth direction simply by changing the wavelength sweep speed.

To perform the polarization adjustment, the polarization state of the reference light LR is adjusted for optimizing the interference efficiency between the measurement light LS and the reference light LR.

(Storage Unit)

The storage unit 212 stores various types of data. Examples of the data stored in the storage unit 212 include image data of an OCT image, image data of a fundus image, image data of an anterior segment image, and subject's eye information. The subject's eye information includes information on the subject such as patient ID and name, and information on the subject's eye such as identification information of the left eye/right eye.

Further, the storage unit 212 stores correction data 212A. The correction data 212A is data for correcting an incident angle (interval of incident angles) of the measurement light at the subject's eye position depending on a deflection angle (interval of deflection angles) of the measurement light by the optical scanner 20. The correction data 212A is data corresponding to change characteristics (deflection operation characteristics) of the deflection angle of the measurement light LS by the optical scanner 20 and change characteristics of the incident angle of the measurement light at the subject's eye position due to the shape of the reflective surface of the ellipsoidal mirror 11. In some embodiments, the storage unit 212 stores a plurality of correction data corresponding to a plurality of scan conditions in which at least one of a deflection angle range and a deflection speed of the optical scanner 20 is different.

In addition, the storage unit 212 stores various kinds of computer programs and data for operating the ophthalmologic apparatus 1.

(Data Processor)

The data processor 230 processes data acquired through photography of the subject's eye E or data acquired through OCT measurement. The data processor 230 includes the image forming unit 231 and a correction unit 232. In some embodiments, the functions of the data processor 230 are realized by one or more processors. In some embodiments, the functions of the data processor 230 are realized by an image forming processor that realizes the function of the image forming unit 231, and a correction processing processor that realizes the function of the correction unit 232.

(Image Forming Unit)

The image forming unit 231 forms an OCT image (image data) of the subject's eye E based on the sampling data obtained by sampling the detection signal from the detector 125 using the DAQ 130. Examples of the OCT image formed by the image forming unit 231 include an A-scan image, a B-scan image (tomographic image), a C-scan image, and the like. As with the conventional swept source OCT, the image formation process includes noise removal (noise reduction), filtering, dispersion compensation, fast Fourier transform (FFT), and the like. In the case of employing an OCT apparatus of another type, the image forming unit 231 performs known processing according to the type employed.

The image forming unit 231 includes, for example, the circuitry described above. Note that "image data" and an "image" based on the image data may not be distinguished from each other in the present specification.

For example, the data processor 230 performs various kinds of image processing and various kinds of analysis processing on the image formed by the image forming unit 231. For example, the data processor 230 performs various types of image correction such as brightness correction. In addition, the data processor 230 can also apply various kinds of image processing and various kinds of analysis processing to the image (e.g., the fundus image, the anterior segment image, or the like) obtained using the imaging optical system (not shown).

The data processor 230 performs known image processing such as interpolation for interpolating pixels in tomographic images to form three-dimensional image data of the fundus Ef Note that image data of a three-dimensional image means image data in which the position of a pixel is defined by a three-dimensional coordinate system. Examples of the image data of the three-dimensional image include image data defined by voxels three-dimensionally arranged. Such image data is referred to as volume data or voxel data. When displaying an image based on volume data, the data processor 230 performs rendering (volume rendering, maximum intensity projection (MIP), etc.) on the volume data, thereby forming image data of a pseudo three-dimensional image viewed from a particular line of sight. The pseudo three-dimensional image is displayed on the display device such as a display unit 240A.

The three-dimensional image data may be stack data of a plurality of tomographic images. The stack data is image data formed by three-dimensionally arranging tomographic images along a plurality of scan lines based on positional relationship of the scan lines. That is, the stack data is image data formed by representing tomographic images, which are originally defined in their respective two-dimensional coordinate systems, by a single three-dimensional coordinate system. That is, the stack data is image data formed by embedding tomographic images into a single three-dimensional space.

The data processor 230 can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired three-dimensional data set (volume data, stack data, etc.). An image in an arbitrary cross section such as the B-mode image or the C-mode image is formed by selecting pixels (voxels) on a designated cross section from the three-dimensional data set. The projection image is formed by projecting the three-dimensional data set in a predetermined direction (z direction, depth direction, axial direction). The shadowgram is formed by projecting a part of the three-dimensional data set (for example, partial data corresponding to a specific layer) in a predetermined direction. An image having a viewpoint on the front side of the subject's eye, such as the C-mode image, the projection image, and the shadowgram, is called a front image (en-face image).

The data processor 230 can build (form) the B-mode image or the front image (blood vessel emphasized image, angiogram) in which retinal blood vessels and choroidal blood vessels are emphasized (highlighted), based on data (for example, B-scan image data) acquired in time series by OCT. For example, the OCT data in time series can be acquired by repeatedly scanning substantially the same site of the subject's eye E.

In some embodiments, the data processor 230 compares the B-scan images in time series acquired by B-scan for substantially the same site, converts the pixel value of a change portion of the signal intensity into a pixel value corresponding to the change portion, and builds the emphasized image in which the change portion is emphasized. Further, the data processor 230 forms an OCTA image by extracting information of a predetermined thickness at a desired site from a plurality of built emphasized images and building as an en-face image.

An image (for example, a three-dimensional image, a B-mode image, a C-mode image, a projection image, a shadowgram, and an OCTA image) generated by the data processor 230 is also included in the OCT image.

Further, the data processor 230 determines the focus state of the measurement light LS in focus adjustment by analyzing the detection result of the interference light obtained by the OCT measurement. For example, the main controller 211 performs repetitive OCT measurements while controlling a focusing driver for driving the focusing lens according to a predetermined algorithm. The data processor 230 analyzes detection results of interference light LC repeatedly acquired by the OCT measurements to calculate predetermined evaluation values relating to image quality of OCT images. The data processor 230 determines whether the calculated evaluation value is equal to or less than a threshold. In some embodiments, the focus adjustment is continued until the calculated evaluation value becomes equal to or less than the threshold. That is, when the evaluation value is equal to or less than the threshold, it is determined that the focus state of the measurement light LS is appropriate. And the focus adjustment is continued until it is determined that the focus state of the measurement light LS is appropriate.

In some embodiments, the main controller 211 monitors the intensity of the interference signal (interference intensity, interference sensitivity) acquired sequentially while acquiring the interference signal by performing the repetitive OCT measurements described above. In addition, while performing this monitoring process, the focusing lens is moved to find the position of the focusing lens in which the interference intensity is maximized. With the focus adjustment thus performed, the focusing lens can be guided to the position where the interference intensity is optimized.

Further, the data processor 230 determines the polarization state of at least one of the measurement light LS and the reference light LR by analyzing the detection result of the interference light obtained by the OCT measurement. For example, the main controller 211 performs repetitive OCT measurements while controlling at least one of the polarization controllers 103 and 118 according to a predetermined algorithm. In some embodiments, the main controller 211 controls the attenuator 120 to change an attenuation of the reference light LR. The data processor 230 analyzes detection results of interference light LC repeatedly acquired by the OCT measurements to calculate predetermined evaluation values relating to image quality of OCT images. The data processor 230 determines whether the calculated evaluation value is equal to or less than a threshold. The threshold is set in advance. Polarization adjustment is continued until the evaluation value calculated becomes equal to or less than the threshold. That is, when the evaluation value is equal to or less than the threshold, it is determined that the polarization state of the measurement light LS is appropriate. And the polarization adjustment is continued until it is determined that the polarization state of the measurement light LS is appropriate.

In some embodiments, the main controller 211 can monitor the interference intensity also in the polarization adjustment.

Further, the data processor 230 performs predetermined analysis processing on the detection result of the interference light acquired by the OCT measurement or the OCT image formed based on the detection result. Examples of the predetermined analysis processing include specifying (identification) of a predetermined site (tissue, lesion) of the subject's eye E; calculation of a distance between designated sites (distance between layers, interlayer distance), area, angle, ratio, or density; calculation by a designated formula; specifying of the shape of a predetermined site; calculation of these statistics; calculation of distribution of the measured value or the statistics; image processing based on these analysis processing results, and the like. Examples of the predetermined tissue include a blood vessel, an optic papilla, a central fovea, a macula, and the like. Examples of the predetermined lesion include a leukoma, a hemorrhage, and the like.

(Correction Unit)

The correction unit 232 generates a new data set group in the A-scan direction, by correcting the data set group in the A-scan direction formed by the image forming unit 231 based on the correction data 212A. In some embodiments, the correction unit 232 can correct at least a part of the data set group in the A-scan direction based on the correction data 212A stored in the storage unit 212 corresponding to the scan condition.

Figure 4:
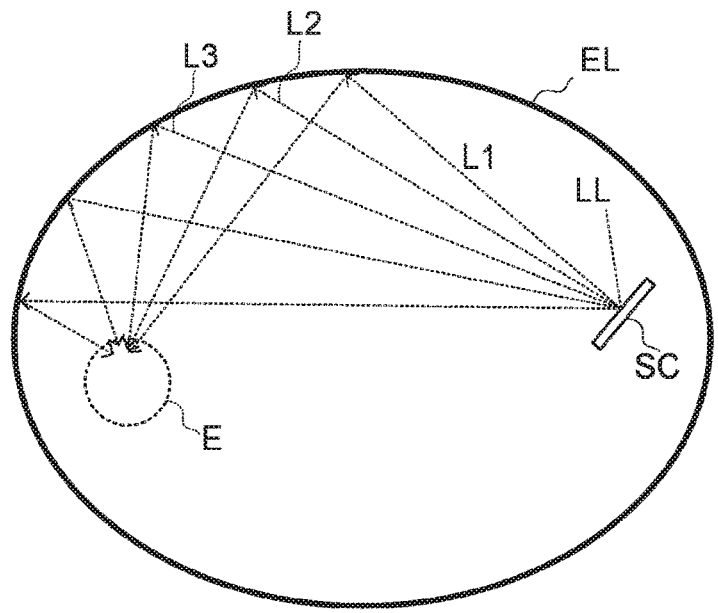
FIG. 4 is a schematic diagram for explaining the relationship between the deflection angle of the measurement light by the optical scanner and the incident angle of the measurement light at the subject's eye position, according to the comparative example of the embodiments.

FIG. 4 shows a diagram for explaining the relationship between the deflection angle of the measurement light by the optical scanner and the incident angle of the measurement light at the subject's eye position, according to the comparative example of the embodiments.

The optical scanner SC deflects light LL from a light source and guide it to a reflective surface of an ellipsoidal mirror EL. The light LL deflected by the optical scanner SC is reflected by the reflective surface of the ellipsoidal mirror EL, and is guided to the subject's eye E. As shown in FIG. 4, even when the light LL is deflected at substantially equal intervals, the following intervals are non-uniform. Here, one of these following intervals is the interval between the incident angle of the light L1 deflected at a first deflection angle and the incident angle of the light L2 deflected at a second deflection angle. Another of these following intervals is the interval between the incident angle of the light L2 deflected at the second deflection angle and the incident angle of the light L3 deflected at a third deflection angle. That is, the deflection angle (interval of deflection angles) by the optical scanner and the incident angle (interval of incident angles) at the subject's eye position have a non-linear relationship.

In the embodiments, by correcting the distortion of the incident angle (interval) based on such a non-linear relationship, a decrease in measurement accuracy based on the deviation of the scan positions can be prevent.

Figure 5:
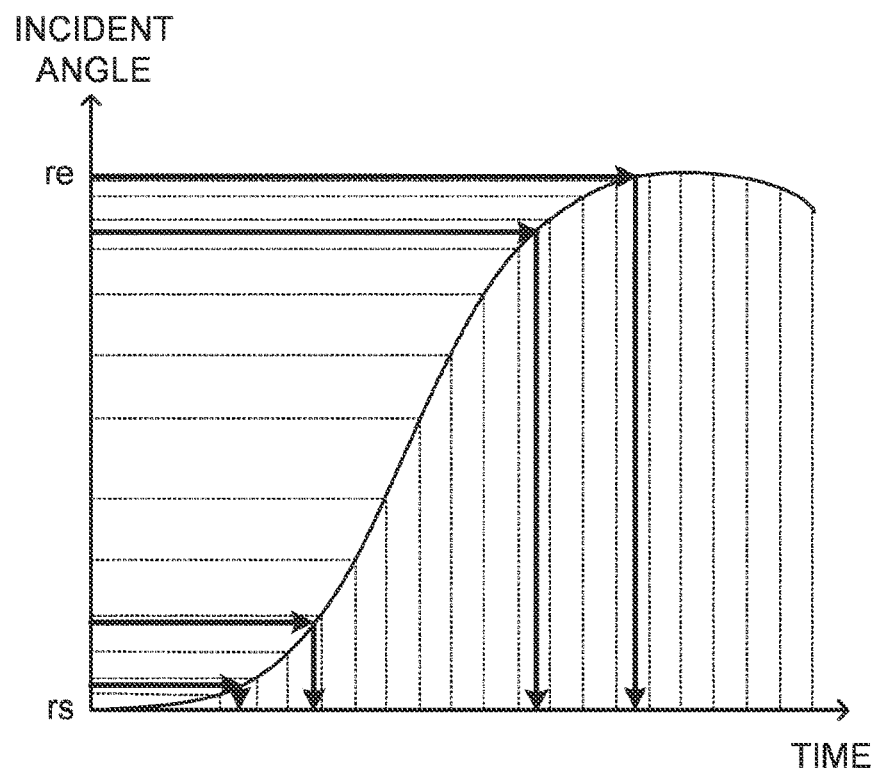
FIG. 5 is a schematic diagram for explaining processing performed by the ophthalmologic apparatus according to the embodiments.
Figure 6:
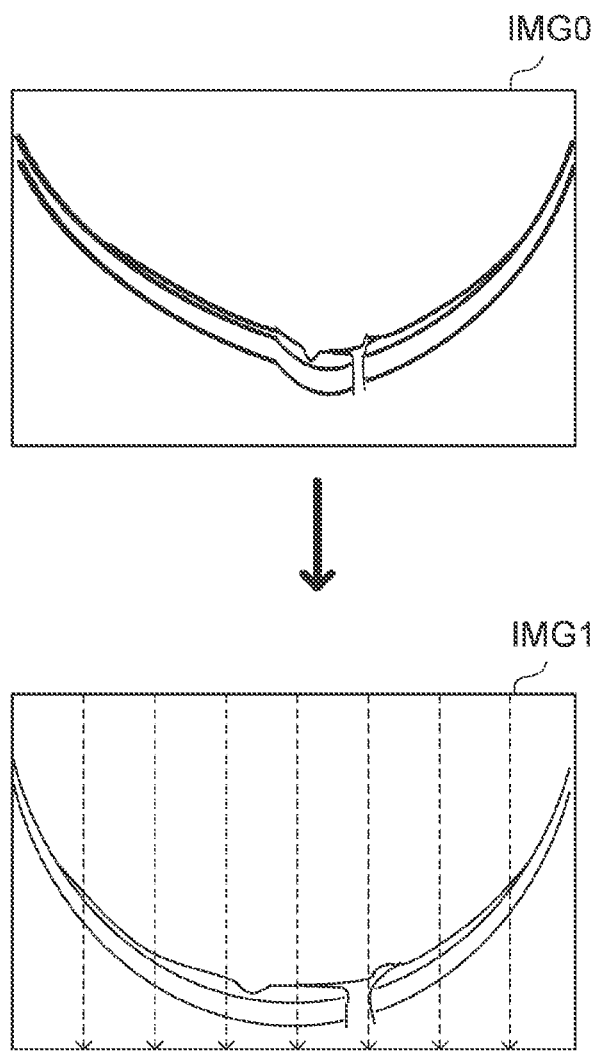
FIG. 6 is a schematic diagram for explaining processing performed by the ophthalmologic apparatus according to the embodiments.

FIGS. 5 and 6 show diagrams describing the operation of the correction unit 232 according to the embodiments. FIG. 5 is a diagram for explaining the correction operation by the correction unit 232. FIG. 5 schematically represents deflection angle versus time characteristics of the optical scanner 20. In FIG. 5, the horizontal axis represents the time corresponding to the execution timing of the A-scan (data set acquisition timing), and the vertical axis represents the incident angle at the subject's eye position. FIG. 6 schematically shows a tomographic image of the fundus Ef of the subject's eye E. It should be noted that the number of A-scans in the tomographic images IMG0 and IMG1 is illustrative in FIG. 6, and is not limited to that number.

The optical scanner 20 includes a mirror that reflects the measurement light LS, for example. The optical scanner 42 deflects the measurement light LS in a predetermined deflection angle range by swinging (rocking) the mirror back and forth in a swing direction corresponding to a predetermined deflection direction. For example, as shown in FIG. 5, the incident angle range is a range between an incident start angle rs (first incident angle) and an incident end angle re (second incident angle). That is, the incident angle range of the measurement light LS deflected by the optical scanner 20 at the subject's eye position includes, as shown in FIG. 5, a linear operation range and non-linear operation range. In the linear operation range, the incident angle changes approximately linearly with changes in the data set acquisition timing (time changes). In the non-linear operation range, the incident angle does not change approximately linearly with changes in the data set acquisition timing. The non-linear operation range includes the incident start angle rs and the incident end angle re.

The tomographic image IMG0 as shown in FIG. 6 is obtained from the data set group in the A-scan direction acquired using the measurement light LS incident on the subject's eye E in the incident angle range shown in FIG. 5. In the tomographic image IMG0 shown in FIG. 6, the intervals between the A scans based on the measurement light incident on the subject's eye are non-uniform. Therefore, in practice, the tomographic image formed using the acquired data set group is distorted due to the above non-linearity.

On the other hand, as shown in FIG. 5, the correction unit 232 corrects the data set group so as to cancel the uneven distribution of the scan positions. That is, the correction unit 232 corrects one or more data sets corresponding to at least a part of a range of the incident angle in the data set group based on the correction data so that the data set group acquired by OCT is a data set group acquired based on the measurement light LS incident at substantially equal intervals in the incident angle range at the subject's eye position.

The tomographic image IMG1 as shown in FIG. 6 is obtained using the new data set group corrected by the correction unit 232. The tomographic image IMG1 shown in FIG. 6 is formed from the data set group acquired using the measurement light LS incident at substantially equal intervals in the incident angle range, regardless of non-linearity described above. Therefore, the formed tomographic image has no distortion caused by the above non-linearity. Thereby, measurement accuracy can be improved.

The correction unit 232 can correct the data set group using various methods.

First Operation Example

Figure 7:
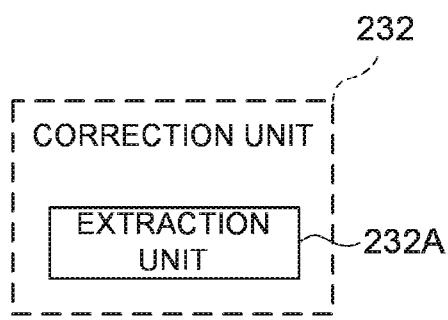
FIG. 7 is a schematic diagram illustrating an example of the configuration of an ophthalmologic apparatus according to the embodiments.

FIG. 7 shows a block diagram of an example of the configuration of the correction unit 232 according to a first operation example of the embodiments.

The correction unit 232 includes an extraction unit 232A. The extraction unit 232A extracts one or more data sets from at least a part of the data set group obtained by performing OCT. The correction unit 232 generates a new data set group by replacing at least a part of the data set group obtained by performing OCT with the one or more data sets extracted by the extraction unit 232A.

Figure 8:
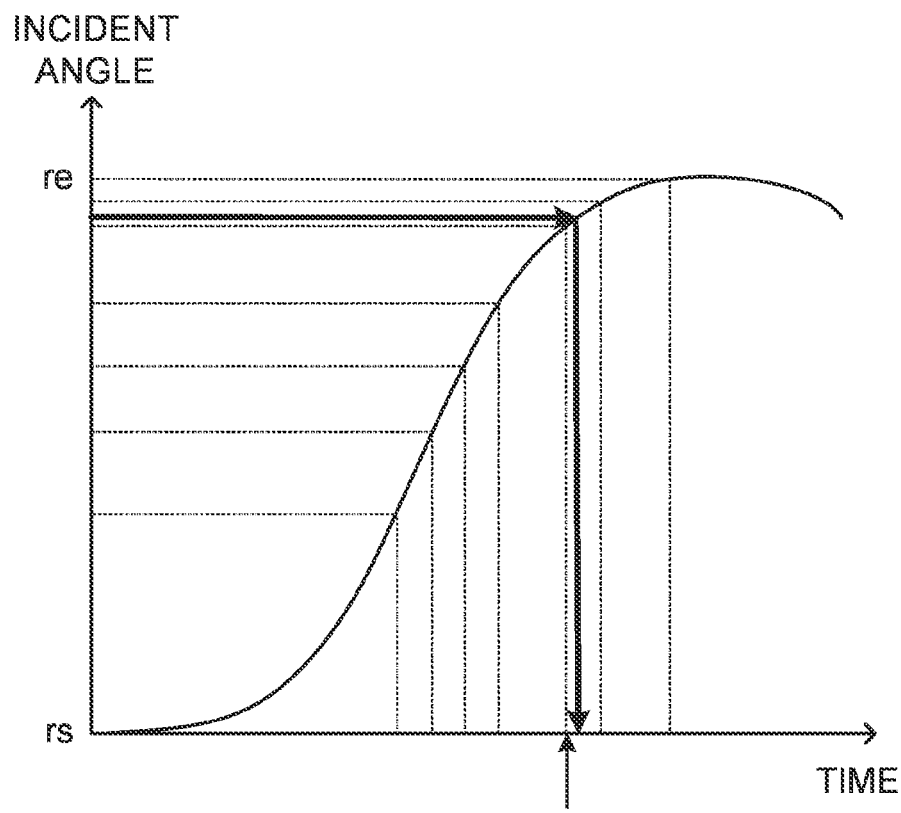
FIG. 8 is a schematic diagram for explaining processing performed by the ophthalmologic apparatus according to the embodiments.

FIG. 8 shows a diagram describing the operation of the correction unit 232 according to the first operation example of the embodiments. In FIG. 8, parts similarly configured to those in FIG. 5 are denoted by the same reference numerals, and the description thereof is omitted unless it is necessary.

The extraction unit 232A extracts one or more data sets so that the incident angles of the measurement light LS at the subject's eye position are arranged at equal intervals. At this time, the extraction unit 232A can extract the closest data set to the data set corresponding to a desired incident angle in the non-linear operation range. That is, the extraction unit 232A can extract the one or more data sets selected by the nearest neighbor method.

Second Operation Example

Figure 9:
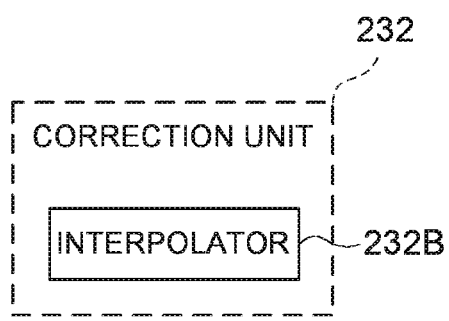
FIG. 9 is a schematic diagram illustrating an example of the configuration of an ophthalmologic apparatus according to the embodiments.

FIG. 9 shows a block diagram of an example of the configuration of the correction unit 232 according to a second operation example of the embodiments.

The correction unit 232 includes an interpolator (interpolation unit) 232B. The interpolator 232B calculates an interpolation data set by interpolating at least a part of the data set group obtained by performing OCT. The correction unit 232 generates a new data set group by replacing at least a part of the data set group obtained by performing OCT with the interpolation data set calculated by the interpolator 232B.

Figure 10:
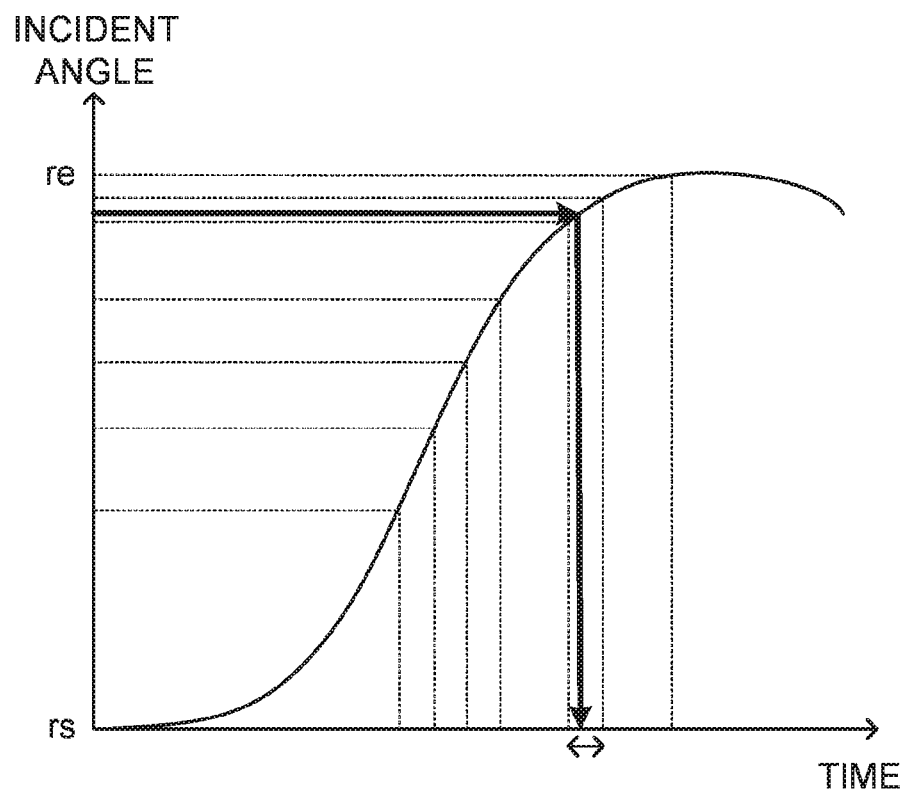
FIG. 10 is a schematic diagram for explaining processing performed by the ophthalmologic apparatus according to the embodiments.

FIG. 10 shows a diagram describing the operation of the correction unit 232 according to the second operation example of the embodiments. In FIG. 10, like reference numerals designate like parts as in FIG. 5, and the same description may not be repeated.

The interpolator 232B calculates an interpolation data set by interpolating at least a part of the data set group obtained by performing OCT so that the incident angles of the measurement light LS at the subject's eye position are arranged at equal intervals. At this time, the interpolator 232B calculates the interpolation data set by linearly interpolating data sets on both sides adjacent to the data set corresponding to a desired incident angle in the non-linear operation range. In some embodiments, the interpolator 232B calculates the interpolation data set by averaging data sets within a predetermined range including the data set corresponding to a desired incident angle in the non-linear operation range.

Third Operation Example

Figure 11:
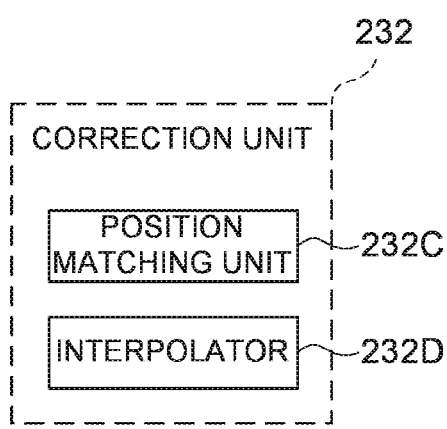
FIG. 11 is a schematic diagram illustrating an example of the configuration of an ophthalmologic apparatus according to the embodiments.

FIG. 11 shows a block diagram of an example of the configuration of the correction unit 232 according to a third operation example of the embodiments.

The correction unit 232 includes a position matching unit (registration) 232C and an interpolator 232D. The position matching unit 232C performs position matching in the A-scan direction on at least a part of the data set group obtained by performing OCT. The interpolator 232D calculates an interpolation data set by interpolating at least a part of the data set group that has been performed position matching by the position matching unit 232C. The correction unit 232 generates a new data set group by replacing at least a part of the data set group obtained by performing OCT with the interpolation data set calculated by the interpolator 232D.

Figure 12:
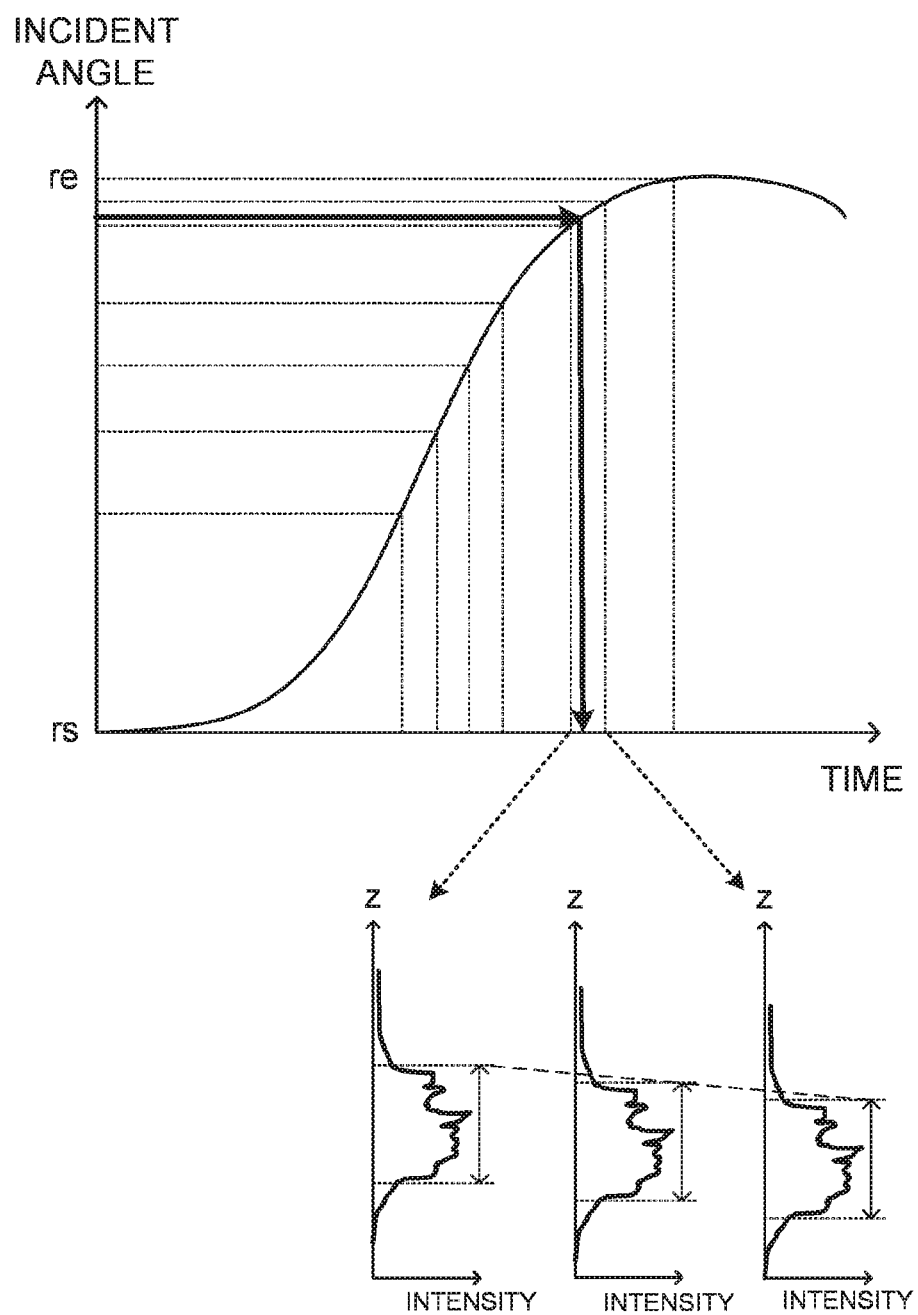
FIG. 12 is a schematic diagram for explaining processing performed by the ophthalmologic apparatus according to the embodiments.

FIG. 12 shows a diagram describing the operation of the correction unit 232 according to the third operation example of the embodiments. FIG. 12 schematically shows the incidence angle versus time characteristics according to the embodiments. In FIG. 12, like reference numerals designate like parts as in FIG. 5, and the same description may not be repeated. FIG. 12 schematically illustrates the operation of the interpolation processing of the data set of the reflection intensity profile data of A line. However, the operation of the interpolation processing of the data set of the A-scan image data is the same.

The position matching unit 232C selects two data sets so that the incident angles are equally spaced in the non-linear operation range in the incident angle versus time characteristics shown in FIG. 12, and specifies a predetermined range in the depth direction for selected two data sets. In some embodiments, the position matching unit 232C specifies the range in the depth direction corresponding to a predetermined layer region by performing segmentation processing. The position matching unit 232C specifies the above range in the depth direction for the two data sets in the non-linear operation range, and specifies z positions of the interpolation data set so that the incident angles are equally spaced. The position matching unit 232C aligns the two data sets in the non-linear operation range to the specified z positions.

The interpolator 232D calculates an interpolation data set by interpolating for the specified range in the depth direction, for the two data sets that have been performed position matching by the position matching unit 232C. At this time, the interpolator 232D calculates the interpolation data set by performing linear interpolation processing, averaging processing, or weighted averaging processing.

Fourth Operation Example

Figure 13:
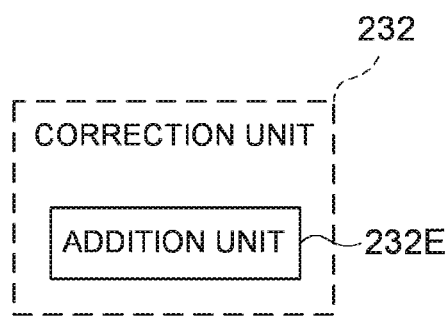
FIG. 13 is a schematic diagram illustrating an example of the configuration of an ophthalmologic apparatus according to the embodiments.

FIG. 13 shows a block diagram of an example of the configuration of the correction unit 232 according to a fourth operation example of the embodiments.

The correction unit 232 includes an addition unit 232E. The addition unit 232E generates a new data set so that the incident angles of the measurement light LS at the subject's eye position are arranged at equal intervals. In some embodiments, the addition unit 232E adds a data set corresponding to an incident angle in the linear operation range in the incident angle versus time characteristics. In some embodiments, the addition unit 232E duplicates the data set of the adjacent A line. That is, the addition unit 232E adds the data set based on the data set corresponding to the incident angle in the linear operation range.

Figure 14:
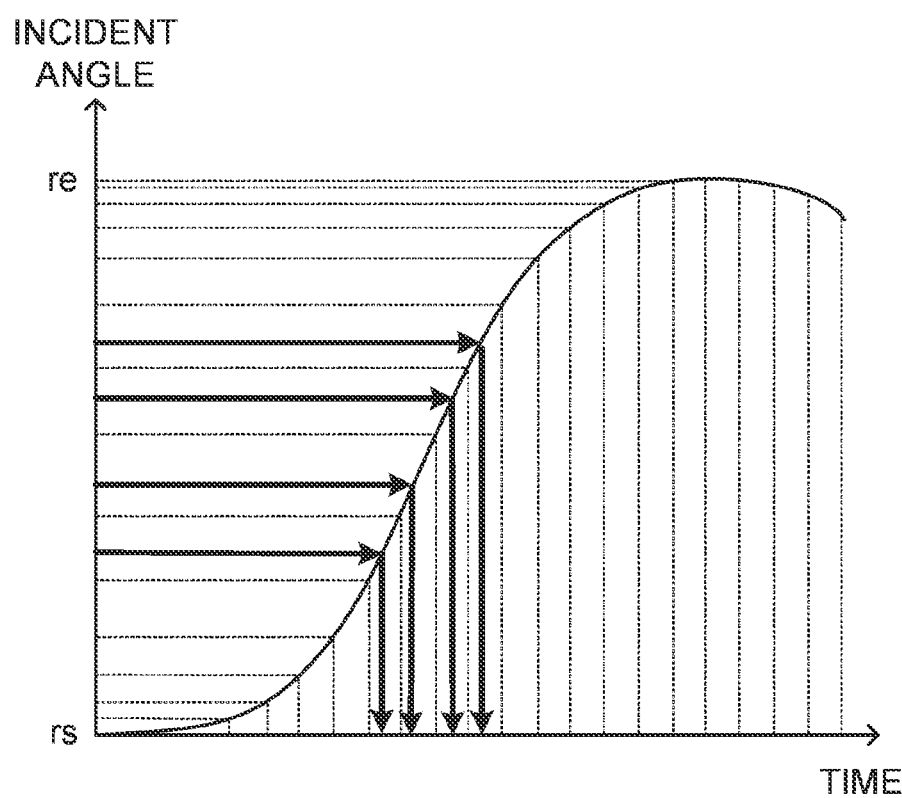
FIG. 14 is a schematic diagram for explaining processing performed by the ophthalmologic apparatus according to the embodiments.

FIG. 14 shows a diagram describing the operation of the correction unit 232 according to the fourth operation example of the embodiments. In FIG. 14, like reference numerals designate like parts as in FIG. 5, and the same description may not be repeated.

The addition unit 232E adds the data set corresponding to the incident angle in the linear operation range so that the incident angles of the measurement light LS at the subject's eye position are arranged at equal intervals. In some embodiments, the correction unit 232 decimates a data set corresponding to the incident angle in the non-linear operation range so that the incident angles are equally spaced.

The data processor 230 that functions as above includes, for example, a processor described above, a RAM, a ROM, a hard disk drive, a circuit board, and the like. Computer programs that cause a processor to execute the above functions are previously stored in a storage device such as a hard disk drive.

(User Interface)

The user interface 240 includes the display unit 240A and an operation unit 240B. The display unit 240A includes the aforementioned display device of the arithmetic control unit 200 and/or the display device 300. The operation unit 240B includes the aforementioned operation device of the arithmetic control unit 200. The operation unit 240B may include various types of buttons and keys provided on the case of the ophthalmologic apparatus 1 or the outside. For example, when the ophthalmologic apparatus 1 has a case similar to that of the conventional fundus camera, the operation unit 240B may include a joy stick, an operation panel, and the like provided to the case. Besides, the display unit 240A may include various types of display devices such as a touch panel and the like arranged on the case of the ophthalmologic apparatus 1.

Note that the display unit 240A and the operation unit 240B need not necessarily be formed as separate devices. For example, a device like a touch panel, which has a display function integrated with an operation function, can be used. In such cases, the operation unit 240B includes the touch panel and a computer program. The content of operation performed on the operation unit 240B is fed to the controller 210 in the morphology of an electrical signal. Moreover, operations and inputs of information may be performed by using a graphical user interface (GUI) displayed on the display unit 240A and the operation unit 240B.

The optical system in the path from the interference optical system included in the OCT unit 100 to the ellipsoidal mirror 11, or these optical systems and the image forming unit 231 are an example of the "data acquisition unit" according to the embodiments.

Operation Example

The operation of the ophthalmologic apparatus 1 according to the embodiments will be described.

In the first operation example, the data set group of the A-scan image data is corrected.

Figure 15:
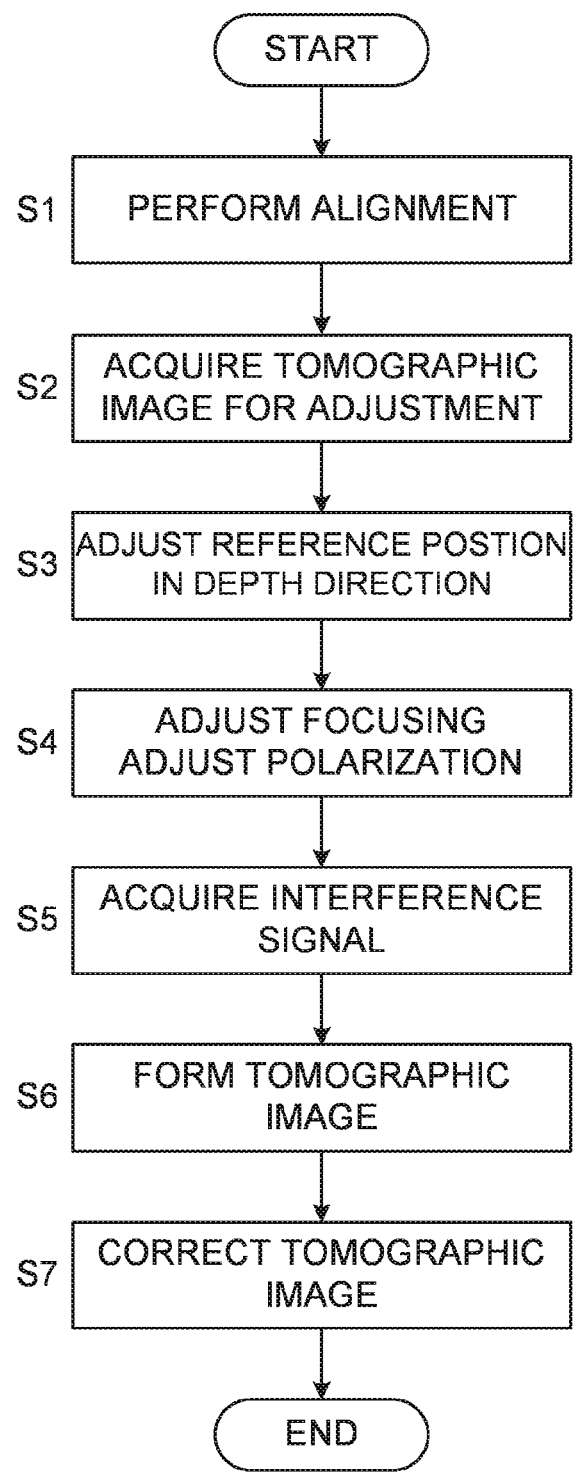
FIG. 15 is a flowchart illustrating an example of the operation of the ophthalmologic apparatus of the embodiments.

FIG. 15 shows a first operation example of the ophthalmologic apparatus 1 according to the embodiments. FIG. 15 shows a flowchart of the first operation example of the ophthalmologic apparatus 1 according to the embodiments. The storage unit 212 stores a of computer programs for realizing the processing shown in FIG. 15. The main controller 211 operates according to the computer programs, and thereby the main controller 211 performs the processing shown in FIG. 15.

(S1: Perform Alignment)

The main controller 211 performs alignment.

That is, the main controller 211 controls the alignment optical system (not shown) to project the alignment indicator onto the subject's eye E. At this time, a fixation target is also projected onto the subject's eye E. The main controller 211 controls the movement mechanism 150 based on the movement amount of the optical system to relatively move the optical system with respect to the subject's eye E by the movement amount. The movement amount is specified based on the receiving light image obtained using the imaging optical system (not shown), for example. The main controller 211 repeatedly executes this processing.

(S2: Acquire Tomographic Image for Adjustment)

The main controller 211 causes the fixation optical system (not shown) to project the fixation target for OCT measurement at a predetermined position.

Subsequently, the main controller 211 controls the OCT unit 100 to perform OCT provisional measurement, and to acquire a tomographic image for adjustment for adjusting the reference position of the measurement range in the depth direction. Specifically, the main controller 211 controls the optical scanner 20 to deflect the measurement light LS generated based on the light L0 emitted from the light source unit 101 and to scan a predetermined site (for example, fundus) of the subject's eye E with the deflected measurement light LS. The detection result of the interference light obtained by scanning with the measurement light LS is sent to the image forming unit 231 after being sampled in synchronization with the clock KC. The image forming unit 231 forms the tomographic image (OCT image) of the subject's eye E from the obtained interference signal.

(S3: Adjust Reference Position in Depth Direction)

Subsequently, the main controller 211 adjusts the reference position of the measurement range in the depth direction (z direction).

For example, the main controller 211 causes the data processor 230 to specify a predetermined site (for example, sclera) in the tomographic image obtained in step S2, and sets a position separated by a predetermined distance in the depth direction from the specified position of the predetermined site as the reference position of the measurement range. Alternatively, a predetermined position determined in advance so that the optical path lengths of the measurement light LS and the reference light LR substantially coincide may be set as the reference position of the measurement range.

(S4: Adjust Focusing, Adjust Polarization)

Next, the main controller 211 perform control of adjusting focusing and of adjusting polarization.

For example, the main controller 211 controls the OCT unit 100 to perform OCT measurement, after controlling the focusing driver (not shown) to move the focusing lens by a predetermined distance. The main controller 211 causes the data processor 230 to determine the focus state of the measurement light LS based on the detection result of the interference light acquired by the OCT measurement, as described above. When it is determined that the focus state is not appropriate based on the determination result of the data processor 230, the main controller 211 controls the focusing driver again and repeats this until it is determined that the focus state of the measurement light LS is appropriate.

Further, for example, the main controller 211 controls the OCT unit 100 to perform OCT measurement after controlling at least one of the polarization controllers 103 and 118 to change the polarization state of at least one of the light L0 and the measurement light LS by a predetermined amount. And then, the main controller 211 causes the image forming unit 231 to form the OCT image on the basis of the detection result of the acquired interference light. The main controller 211 causes the data processor 230 to determine the image quality of the OCT image acquired by the OCT measurement, as described above. When it is determined that the polarization state is not appropriate based on the determination result of the data processor 230, the main controller 211 controls the polarization controllers 103 and 118 again and repeats this until it is determined that the polarization state of the measurement light LS is appropriate.

(S5: Acquire Interference Signal)

Subsequently, the main controller 211 controls the OCT unit 100 to perform OCT measurement. The detection result of the interference light acquired by the OCT measurement is sampled by the DAQ 130 and is stored as the interference signal in the storage unit 212 or the like.

(S6: Form Tomographic Image)

Next, the main controller 211 causes the image forming unit 231 to form the data set group of the A-scan image data of the subject's eye E based on the interference signal acquired in step S5.

(S7: Correct Tomographic Image)

The main controller 211 causes the correction unit 232 to generate a new data set group by correcting at least a part of the data set group of the A-scan image data formed in step S6, based on the correction data 212A stored in the storage unit 212. The main controller 211 can cause the display unit 240A to display the B-scan image (tomographic image IMG1 of FIG. 6) based on the data set group of the newly generated A-scan image data.

This terminates the operation of the ophthalmologic apparatus 1 (END).

In the second operation example, the data set group of the reflection intensity profile data is corrected.

Figure 16:
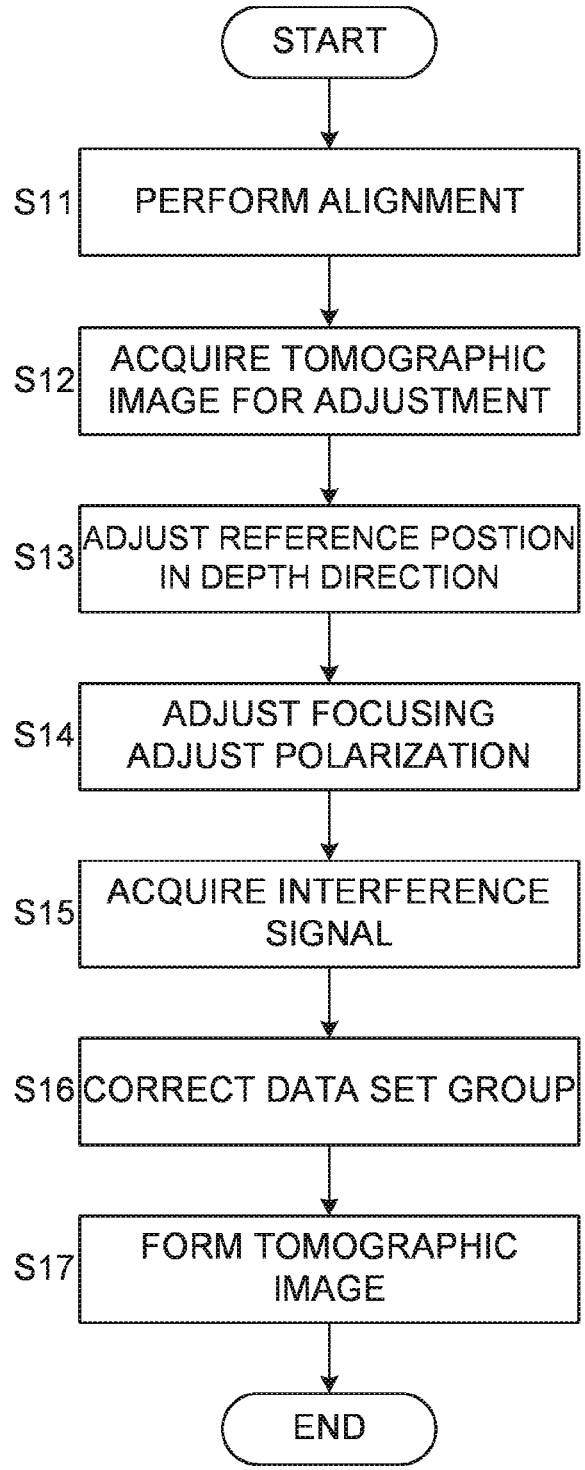
FIG. 16 is a flowchart illustrating an example of the operation of the ophthalmologic apparatus of the embodiments.

FIG. 16 shows a second operation example of the ophthalmologic apparatus 1 according to the embodiments. FIG. 16 shows a flowchart of the second operation example of the ophthalmologic apparatus 1 according to the embodiments. The storage unit 212 stores a computer program for realizing the processing shown in FIG. 16. The main controller 211 operates according to the computer programs, and thereby the main controller 211 performs the processing shown in FIG. 16.

(S11: Perform Alignment)

The main controller 211 performs alignment, in the same manner as step S1.

(S12: Acquire Tomographic Image for Adjustment)

The main controller 211 controls the OCT unit 100 to perform OCT provisional measurement, and to acquire a tomographic image for adjustment for adjusting the reference position of the measurement range in the depth direction, in the same manner as step S2.

(S13: Adjust Reference Position in Depth Direction)

Subsequently, the main controller 211 adjusts the reference position of the measurement range in the depth direction (z direction), in the same manner as step S3.

(S14: Adjust Focusing, Adjust Polarization)

Next, the main controller 211 performs control of adjusting focusing and of adjusting polarization, in the same manner as step S4.

(S15: Acquire Interference Signal)

Subsequently, the main controller 211 controls the OCT unit 100 to perform OCT measurement, in the same manner as step S5.

(S16: Correct Data Set Group)

The main controller 211 causes the correction unit 232 to generate a new data set group by correcting at least a part of the data set group of the reflection intensity profile data acquire in step S15, based on the correction data 212A stored in the storage unit 212.

(S17: Form Tomographic Image)

Next, the main controller 211 causes the image forming unit 231 to form the data set group of the A-scan image data of the subject's eye E based on the new data set group of the new reflection intensity profile data generated in step S16. The main controller 211 can cause the display unit 240A to display the B-scan image (tomographic image IMG1 of FIG. 6) based on the data set group of the A-scan image data formed by the image forming unit 231.

This terminates the operation of the ophthalmologic apparatus 1 (END).

MODIFICATION EXAMPLE

First Modification Example

In the above embodiments, in the case that the optical scanner 20 includes the first galvano scanner and the second galvano scanner, the storage unit 212 may store correction data for each galvano scanner. In the following, the configuration of the ophthalmologic apparatus according to the first modification example of the embodiments will be described focusing on the differences from the configuration of the ophthalmologic apparatus 1 according to the embodiments.

Figure 17:
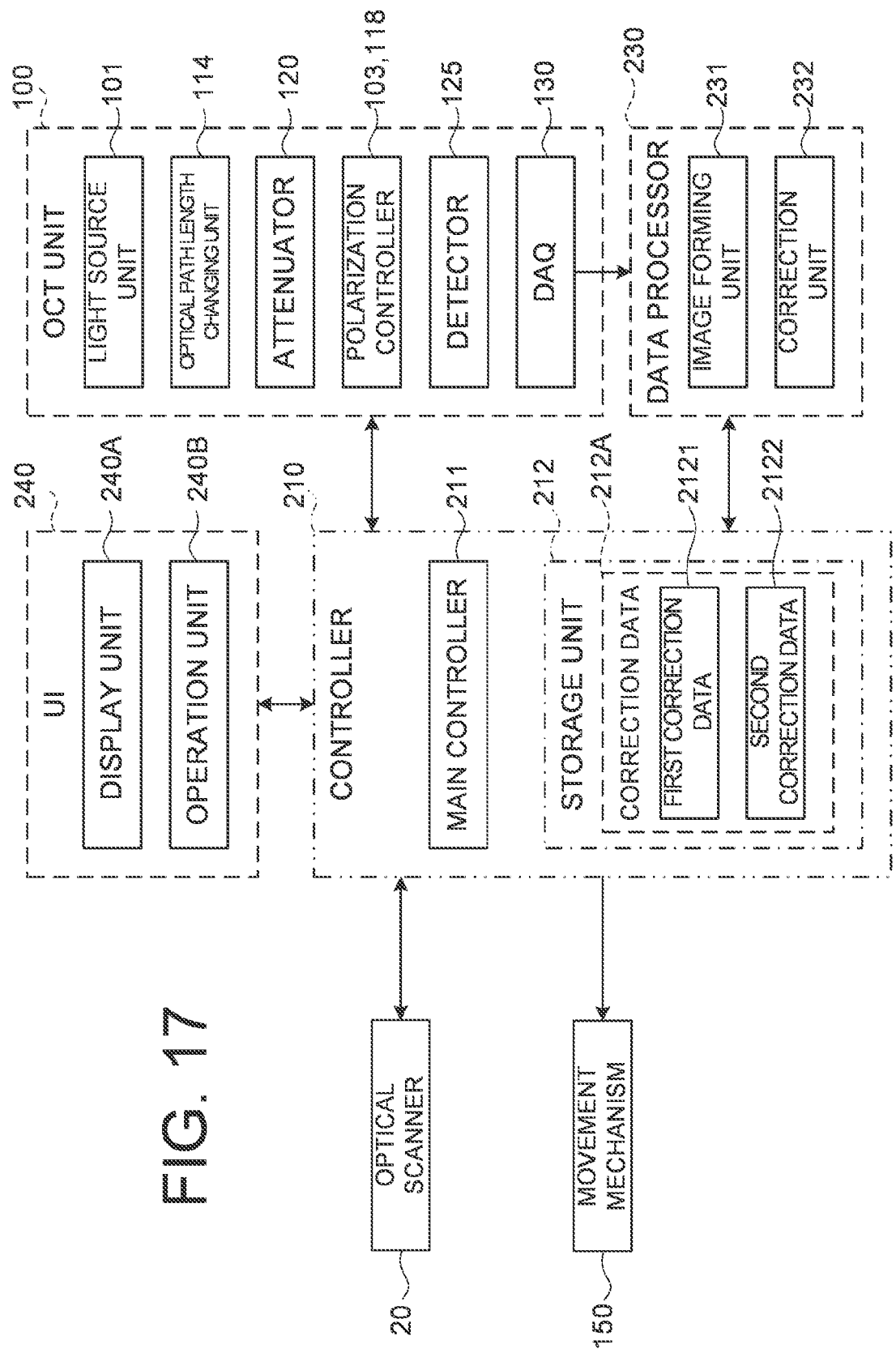
FIG. 17 is a schematic block diagram illustrating an example of the configuration of the ophthalmologic apparatus according to a modification example of the embodiments.

FIG. 17 shows a block diagram of an example of the configuration of the ophthalmologic apparatus according to the first modification example of the embodiments. In FIG. 17, components similar to those in FIG. 3 are given the same reference numerals. The description of such components is basically omitted.

The difference between the configuration of the ophthalmologic apparatus of the first modification example of the embodiments and the configuration of the ophthalmologic apparatus 1 according to the embodiments shown in FIG. 3 is correction data 212A stored in the storage unit 212. The correction data 212A includes a first correction data 2121 and a second correction data 2122.

The first correction data 2121 is correction data for correcting an incident angle (interval of incident angles) of the measurement light LS at the subject's eye position depending on a deflection angle of the measurement light LS deflected by the first galvano scanner. The second correction data 2122 is correction data for correcting an incident angle (interval of incident angles) of the measurement light LS at the subject's eye position depending on a deflection angle of the measurement light LS deflected by the second galvano scanner. Similar to the correction data 212A, the first correction data 2121 is data corresponding to change characteristics (deflection operation characteristics) of the deflection angle of the measurement light LS by the first galvano scanner and change characteristics of the incident angle of the measurement light at the subject's eye position due to the shape of the reflective surface of the ellipsoidal mirror 11. Similar to the correction data 212A, the second correction data 2122 is data corresponding to change characteristics (deflection operation characteristics) of the deflection angle of the measurement light LS by the second galvano scanner and change characteristics of the incident angle of the measurement light at the subject's eye position due to the shape of the reflective surface of the ellipsoidal mirror 11. The correction unit 232 is capable of switching one of correction processing for at least a part of the data set group based on the first correction data 2121 and correction processing for at least a part of the data set group based on the second correction data 2122, and of performing the switched correction processing.

In the OCT measurement, a measurement site is scanned in various scan modes. Deflection angle ranges and deflection speeds are different each other depending on the scan region and/or scan pattern. Thereby, depending on the scan condition, one of the first galvano scanner and the second galvano scanner is controlled to operate at high speed, and the other is controlled to operate at low speed. According to the first modification example, the data set group can be corrected for the deflection angle of one of the first galvano scanner and the second galvano scanner according to the scan condition.

Second Modification Example

In the above embodiments or the first modification example, the case in which the optical system 10 includes the optical scanner 20 and the ellipsoidal mirror 11 has been described. However, the configuration of the ophthalmologic apparatus according to the embodiments is not limited thereto. In the ophthalmologic apparatus according to the embodiments, the optical system may include a plurality of ellipsoidal mirrors (concave mirrors). In the following, the configuration of the ophthalmologic apparatus according to a second modification example of the embodiments will be described focusing on the differences from the configuration of the ophthalmologic apparatus 1 according to the embodiments.

Figure 18:
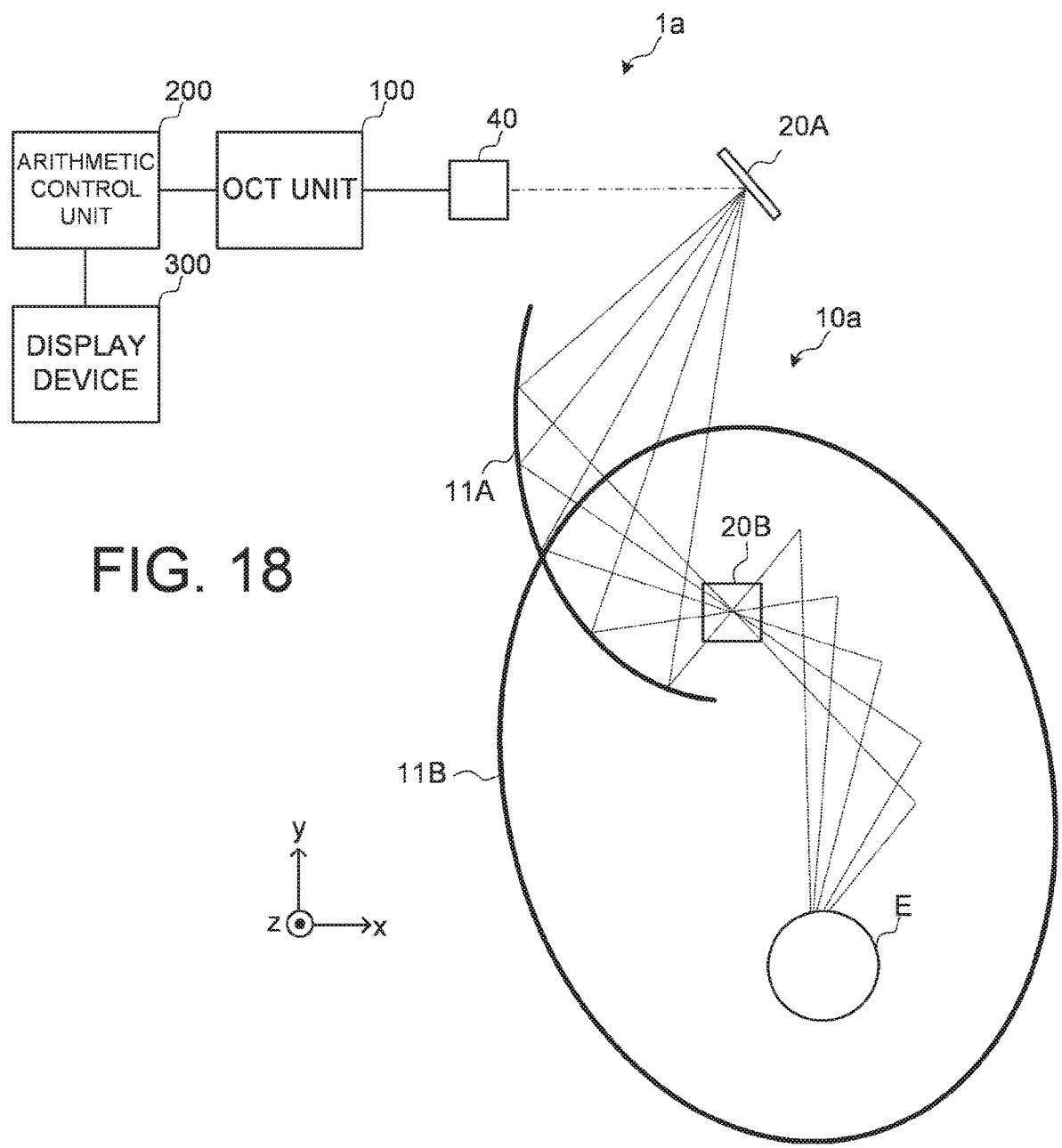
FIG. 18 is a schematic diagram illustrating an example of the configuration of the ophthalmologic apparatus according to a modification example of the embodiments.

FIG. 18 shows an example of the configuration of the ophthalmologic apparatus according to the second modification example of the embodiments. In FIG. 18, like reference numerals designate like parts as in FIG. 1, and the same description may not be repeated.

The configuration of an ophthalmologic apparatus 1a according to the second modification example of the embodiments is different from that of the ophthalmologic apparatus 1 according to the embodiments shown in FIG. 1 in that an optical system 10a is provided instead of the optical system 10. The optical system 10a includes optical scanners 20A and 20B, and ellipsoidal mirrors 11A and 11B. The optical scanner 20A deflects, for example, the measurement light LS so as to scan a photographing (imaging) site in the horizontal direction orthogonal to the optical path (optical axis) of the measurement light LS. The optical scanner 20B deflects, for example, the measurement light LS deflected by the optical scanner 20A so as to scan the photographing site in the vertical direction orthogonal to the optical path (optical axis) LS of the measurement light LS. In some embodiments, the optical system 10a includes a concave mirror whose reflective surface is formed in a concave shape, instead of at least one of the ellipsoidal mirrors 11A and 11B. In some embodiments, the reflective surface of the concave mirror is formed to be a free-form surface.

The ellipsoidal mirror 11A has two optically conjugate focal points (third focal point, fourth focal point), similar to the ellipsoidal mirror 11. The ellipsoidal mirror 11B has two optically conjugate focal points (fifth focal point, sixth focal point), similar to the ellipsoidal mirror 11. The optical scanner 20A (deflected surface of the optical scanner 20A) is disposed at the third focal point of the ellipsoidal mirror 11A, near the third focal point, a position optically conjugate with the third focal point (conjugate position of the third focal point), or near the position optically conjugate with the third focal point. The optical scanner 20B (deflected surface of the optical scanner 20B) is disposed at the fourth focal point of the ellipsoidal mirror 11A, near the fourth focal point, a position optically conjugate with the fourth focal point (conjugate position of the fourth focal point), or near the position optically conjugate with the fourth focal point. The optical scanner 20B (deflected surface of the optical scanner 20B) is disposed at the fifth focal point of the ellipsoidal mirror 11B, near the fifth focal point, a position optically conjugate with the fifth focal point (conjugate position of the fifth focal point), or near the position optically conjugate with the fifth focal point. The subject's eye position, where the subject's eye E (pupil) is arranged, is disposed at the sixth focal point of the ellipsoidal mirror 11B, near the sixth focal point, a position optically conjugate with the sixth focal point (conjugate position of the sixth focal point), or near the position optically conjugate with the sixth focal point.

The correction data 212A according to the second modification example is data for correcting an incident angle (interval of incident angles) of the measurement light LS with respect to the optical scanner 20B depending on a deflection angle of the measurement light LS deflected by the optical scanner 20A. The optical scanner 20B and the subject's eye position have a conjugate relationship. Therefore, the correction data 212A according to the second modification example is data for correcting an incident angle of the measurement light LS at the subject's eye position depending on a deflection angle of the measurement light LS deflected by the optical scanner 20A.

Further, the correction data 212A according to the second modification example may be data for correcting an incident angle of the measurement light LS at the subject's eye position depending on a deflection angle of the measurement light LS deflected by the optical scanner 20B.

Similar to the embodiments, the ophthalmologic apparatus 1a having such a configuration can form an OCT image of the subject's eye E according to the flow shown in FIG. 15 or FIG. 16.

In the embodiments described above or the modification examples thereof, the case where the optical scanner 20 includes a galvano scanner has been described. However, the configuration according to the embodiments or the modification examples thereof is not limited thereto. For example, the optical scanner 20 may include a resonant mirror, a polygon mirror, or the like.

[Effects]

The ophthalmologic apparatus and the method of controlling the ophthalmologic apparatus according to the embodiments are explained.

An ophthalmologic apparatus (1, 1a) according to some embodiments includes a data acquisition unit (optical system in the path from the interference optical system included in the OCT unit 100 to the ellipsoidal mirror 11, 11A, or 11B, or these optical systems and the image forming unit 231), a storage unit (212), and a correction unit (232). The data acquisition unit includes a concave mirror (ellipsoidal mirror 11, 11A, 11B) and an optical scanner (20, 20A, 20B) configured to deflect light (measurement light LS) from a light source to guide to a reflective surface of the concave mirror. The data acquisition unit is configured to acquire a first data set group in an A-scan direction by performing optical coherence tomography on a subject's eye (E) placed at a subject's eye position or a conjugate position of the subject's eye position using light reflected by the reflective surface. The storage unit is configured to store correction data (212A) for correcting an incident angle of the light at the subject's eye position depending on a deflection angle of the light by the optical scanner. The correction unit is configured to generate a second data set group by correcting at least a part of the first data set group based on the correction data stored in the storage unit.

According to such a configuration, a data set group in the A-scan direction can be acquired in consideration of the change characteristics (deflection operation characteristics) of the deflection angle of the optical scanner and the change characteristics of the incident angle of the measurement light at the subject's eye position due to the shape of the reflective surface of the concave mirror. For example, a data set group at the uniformly arranged scan positions can be generated from the data set group acquired at the unevenly distributed scan positions due to the reflection from the reflective surface of the concave mirror. Further, for example, a data set group based on the measurement light incident on the subject's eye at the subject's eye position at intervals of substantially equal incident angle can be acquired. Further, for example, a data set group acquired at high density only at a desired site can be generated from the data set group acquired at the unevenly distributed scan positions due to the reflection from the reflective surface of the concave mirror. As a result, measurement can be performed with a wider angle and higher accuracy using the concave mirror.

In some embodiments, the concave mirror is an ellipsoidal mirror (11, 11A, 11B), the optical scanner is disposed at a first focal point (third focal point, fifth focal point) of the ellipsoidal mirror, near the first focal point, a conjugate position of the first focal point, or near the conjugate position of the first focal point, and the subject's eye position is disposed at a second focal point (fourth focal point, sixth focal point) of the ellipsoidal mirror, near the second focal point, a conjugate position of the second focal point, or near the conjugate position of the second focal point.

According to such a configuration, a data set group at the uniformly arranged scan positions can be generated from the data set group acquired at the unevenly distributed scan positions due to the reflection from the reflective surface of the ellipsoidal mirror. Further, for example, a data set group based on the measurement light incident on the subject's eye at the subject's eye position at intervals of substantially equal incident angle can be acquired. Further, for example, a data set group acquired at high density only at a desired site can be generated from the data set group acquired at the unevenly distributed scan positions due to the reflection from the reflective surface of the ellipsoidal mirror. As a result, measurement can be performed with a wider angle and higher accuracy using the ellipsoidal mirror.

In some embodiments, the correction unit is configured to correct one or more data sets corresponding to at least a part of a range of the incident angle in the first data set group so that the first data set group is a data set group acquired based on measurement light incident at substantially equal intervals at the subject's eye position.

According to such a configuration, a data set group at the uniformly arranged scan positions can be generated from the data set group acquired at the unevenly distributed scan positions due to the reflection from the reflective surface of the concave mirror. Thereby, measurement can be performed with a wider angle and higher accuracy using the concave mirror.

In some embodiments, the correction unit includes an extraction unit (232A) configured to extract one or more data sets from at least a part of the first data set group, and is configured to replace the at least a part of the first data set group with the one or more data sets.

According to such a configuration, a data set group at a desired positions can be acquired from the data set group acquired at the unevenly distributed scan positions by performing simple extraction processing on the data set group.

In some embodiments, the correction unit includes an interpolator (232B) configured to calculate an interpolation data set by interpolating at least a part of the first data set group, and is configured to replace the at least a part of the first data set group with the interpolation data set calculated by the interpolator.

According to such a configuration, a data set group at a desired positions can be acquired from the data set group acquired at the unevenly distributed scan positions by performing simple interpolation processing on the data set group.

In some embodiments, the correction unit includes: a position matching unit (232C) configured to perform position matching in the A-scan direction on at least a part of the first data set group; and an interpolator (232D) configured to calculate an interpolation data set by interpolating at least a part of the first data set group that has been performed position matching by the position matching unit, and the correction unit is configured to replace the at least a part of the first data set group with the interpolation data set calculated by the interpolator.

According to such a configuration, a data set group at a desired positions can be acquired from the data set group acquired at the unevenly distributed scan positions by performing simple position matching (registration) processing and the interpolation processing on the data set group.

In some embodiments, the correction unit is configured to add a new data set to the first data set group.

According to such a configuration, a data set group at a desired positions can be acquired from the data set group acquired at the unevenly distributed scan positions by performing simple addition processing on the data set group.

In some embodiments, the new data set is generated based on at least a part of the first data set group.

According to such a configuration, the new data set is obtained based on the at least a part of the first data set group, and the obtained new data set is added. Thereby, addition processing can be performed on the data set group with simple processing.

In some embodiments, the optical scanner includes: a first scanner configured to deflect the light in a first deflection direction; and a second scanner configured to deflect the light in a second deflection direction toward the subject's eye, the light being deflected by the first scanner, and the correction unit is configured to be capable of switching one of correction processing for at least a part of the first data set group based on first correction data for correcting the incident angle depending on the deflection angle of the light deflected by the first scanner and correction processing for at least a part of the first data set group based on second correction data for correcting the incident angle depending on the deflection angle of the light deflected by the second scanner, and of performing the switched correction processing.

According to such a configuration, the data set group can be corrected with respect to the non-linearity between the deflection angle of one of the first scanner and the second scanner and the incident angle at the subject's eye position, depending on the scan condition. Thereby, the accuracy of OCT measurement performed in various scan modes can be improved.

In some embodiments, the storage unit is configured to store a plurality of correction data corresponding to a plurality of scan conditions in which at least one of a deflection angle range and a deflection speed of the optical scanner is different, and the correction unit is configured to correct at least a part of the first data set group based on the correction data stored in the storage unit corresponding to the scan condition.

According to such a configuration, the second data set group can be generated by correcting at least a part of the first data set group based on the correction data corresponding to the scan condition. Thereby, even when the scan conditions are different, a data set group can be acquired in consideration of non-linearity between the deflection angle of the optical scanner and the incident angle at the subject's eye position.

The ophthalmologic apparatus according to some embodiments further includes an image forming unit (231) configured to form a tomographic image of the subject's eye based on the second data set group generated by the correction unit.

According to such a configuration, the new data set group can be generated by correcting the data set group of the reflection intensity profile data in the A-scan direction depending on the non-linearity between the deflection angle of the optical scanner and the incident angle at the subject's eye position.

Some embodiments are a method of controlling an ophthalmologic apparatus (1, 1a) including a concave mirror (ellipsoidal mirror 11, 11A, 11B) and an optical scanner (20, 20A, 20B) configured to deflect light (measurement light LS) from a light source to guide to a reflective surface of the concave mirror. The method of controlling the ophthalmologic apparatus includes: a data acquisition step of acquiring a first data set group in an A-scan direction by performing optical coherence tomography on a subject's eye (E) placed at a subject's eye position or a conjugate position of the subject's eye position using light reflected by the reflective surface; and a correction step of generating a second data set group by correcting at least a part of the first data set group based on correction data for correcting an incident angle of the light at the subject's eye position depending on a deflection angle of the light by the optical scanner.

According to such a method, a data set group in the A-scan direction can be acquired in consideration of the change characteristics (deflection operation characteristics) of the deflection angle of the optical scanner and the change characteristics of the incident angle of the measurement light at the subject's eye position due to the shape of the reflective surface of the concave mirror. For example, a data set group at the uniformly arranged scan positions can be generated from the data set group acquired at the unevenly distributed scan positions due to the reflection from the reflective surface of the concave mirror. Further, for example, a data set group based on the measurement light incident on the subject's eye at the subject's eye position at intervals of substantially equal incident angle can be acquired. Further, for example, a data set group acquired at high density only at a desired site can be generated from the data set group acquired at the unevenly distributed scan positions due to the reflection from the reflective surface of the concave mirror. As a result, measurement can be performed with a wider angle and higher accuracy using the concave mirror.

In some embodiments, the concave mirror is an ellipsoidal mirror (11, 11A, 11B), the optical scanner is disposed at a first focal point (third focal point, fifth focal point) of the ellipsoidal mirror, near the first focal point, a conjugate position of the first focal point, or near the conjugate position of the first focal point, and the subject's eye position is disposed at a second focal point (fourth focal point, sixth focal point) of the ellipsoidal mirror, near the second focal point, a conjugate position of the second focal point, or near the conjugate position of the second focal point.

According to such a method, a data set group at the uniformly arranged scan positions can be generated from the data set group acquired at the unevenly distributed scan positions due to the reflection from the reflective surface of the ellipsoidal mirror. Further, for example, a data set group based on the measurement light incident on the subject's eye at the subject's eye position at intervals of substantially equal incident angle can be acquired. Further, for example, a data set group acquired at high density only at a desired site can be generated from the data set group acquired at the unevenly distributed scan positions due to the reflection from the reflective surface of the ellipsoidal mirror. As a result, measurement can be performed with a wider angle and higher accuracy using the ellipsoidal mirror.

In some embodiments, the correction step corrects one or more data sets corresponding to at least a part of a range of the incident angle in the first data set group so that the first data set group is a data set group acquired based on light incident at substantially equal intervals at the subject's eye position.

According to such a method, a data set group at the uniformly arranged scan positions can be generated from the data set group acquired at the unevenly distributed scan positions due to the reflection from the reflective surface of the concave mirror. Thereby, measurement can be performed with a wider angle and higher accuracy using the concave mirror.

In some embodiments, the optical scanner includes: a first scanner configured to deflect the light in a first deflection direction; and a second scanner configured to deflect the light in a second deflection direction toward the subject's eye, the light being deflected by the first scanner. The correction step is capable of switching one of correction processing for at least a part of the first data set group based on first correction data for correcting the incident angle depending on the deflection angle of the light deflected by the first scanner and correction processing for at least a part of the first data set group based on second correction data for correcting the incident angle depending on the deflection angle of the light deflected by the second scanner, and of performing the switched correction processing.

According to such a method, the data set group can be corrected with respect to the non-linearity between the deflection angle of one of the first scanner and the second scanner and the incident angle at the subject's eye position, depending on the scan condition. Thereby, the accuracy of OCT measurement performed in various scan modes can be improved.

The method of controlling the ophthalmologic apparatus according to some embodiments further includes an image forming step of forming a tomographic image of the subject's eye based on the second data set group generated in the correction step.

According to such a method, the new data set group can be generated by correcting the data set group of the reflection intensity profile data in the A-scan direction depending on the non-linearity between the deflection angle of the optical scanner and the incident angle at the subject's eye position.

<Others>

The above-described some embodiments or the modification examples thereof are merely examples for carrying out the present invention. Those who intend to implement the present invention can apply any modification, omission, addition, or the like within the scope of the gist of the present invention.

In the embodiments described above or the modification examples thereof, the case where the ophthalmologic apparatus can perform OCT has been described. However, the configuration according to the embodiments or the modification examples thereof is not limited thereto. The embodiments described above or the modification examples thereof can be applied to an ophthalmologic apparatus including a scanning laser ophthalmoscope (SLO) using an ellipsoidal mirror or a concave mirror. The SLO is an apparatus configured to form an image of the subject's eye (for example, fundus) by scanning the subject's eye with light from a light source to detect returning light of the light with a light receiving device. That is, the ophthalmologic apparatus includes a data acquisition unit, a storage unit, and a correction unit. The data acquisition unit includes a concave mirror and an optical scanner configured to deflect light from a light in a predetermined deflection angle range to guide to a reflective surface of the concave mirror. The data acquisition unit is configured to irradiate the subject's eye placed at the subject's eye position or a conjugate position of the subject's eye position with light reflected by the reflective surface, and to acquire a first data set group of the subject's eye based on returning light thereof. The storage unit is configured to store correction data for correcting an incident angle of the light at the subject's eye position depending on a deflection angle of the light by the optical scanner. The correction unit is configured to generate a second data set group by correcting at least a part of the first data set group based on the correction data stored in the storage unit.

In some embodiments, a program for causing a computer to execute the method for controlling the ophthalmologic apparatus is provided. Such a program can be stored in any kind of recording medium that can be read by the computer. Examples of the recording medium can include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide* v. *DIRECTV*, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus, comprising:
a data acquisition unit including a concave mirror and an optical scanner configured to deflect light from a light source to guide to a reflective surface of the concave mirror, and configured to acquire a first data set group in an A-scan direction by performing optical coherence tomography on a subject's eye placed at a subject's eye position or a conjugate position of the subject's eye position using light reflected by the reflective surface;
a storage unit including a memory and configured to store correction data for correcting an incident angle of the light at the subject's eye position depending on a deflection angle of the light by the optical scanner; and
a correction unit including processing circuitry configured to generate a second data set group by correcting at least a part of the first data set group based on the correction data stored in the storage unit,
wherein the processing circuitry in the correction unit is further configured to correct one or more data sets corresponding to at least a part of a range of the incident angle in the first data set group so that the first data set group is a data set group acquired based on measurement light incident at substantially equal intervals at the subject's eye position.

2. The ophthalmologic apparatus of claim 1, wherein
the concave mirror is an ellipsoidal mirror,
the optical scanner is disposed at a first focal point of the ellipsoidal mirror, near the first focal point, a conjugate position of the first focal point, or near the conjugate position of the first focal point, and
the subject's eye position is disposed at a second focal point of the ellipsoidal mirror, near the second focal point, a conjugate position of the second focal point, or near the conjugate position of the second focal point.

3. The ophthalmologic apparatus of claim 1, wherein
the processing circuitry in the correction unit is further configured as an extraction unit configured to extract one or more data sets from at least a part of the first data set group, and is configured to replace the at least a part of the first data set group with the one or more data sets.

4. The ophthalmologic apparatus of claim 1, wherein
the processing circuitry in the correction unit is further configured as an interpolator configured to calculate an interpolation data set by interpolating at least a part of the first data set group, and is configured to replace the at least a part of the first data set group with the interpolation data set calculated by the interpolator.

5. The ophthalmologic apparatus of claim 1, wherein
the processing circuitry in the correction unit is further configured as:
a position matching unit configured to perform position matching in the A-scan direction on at least a part of the first data set group; and
an interpolator configured to calculate an interpolation data set by interpolating at least a part of the first data set group that has been performed position matching by the position matching unit, and
the processing circuitry in the correction unit is configured to replace the at least a part of the first data set group with the interpolation data set calculated by the interpolator.

6. The ophthalmologic apparatus of claim 1, wherein
the processing circuitry in the correction unit is configured to add a new data set to the first data set group.

7. The ophthalmologic apparatus of claim 6, wherein
the new data set is generated based on at least a part of the first data set group.

8. An ophthalmologic apparatus, comprising:
a data acquisition unit including a concave mirror and an optical scanner configured to deflect light from a light source to guide to a reflective surface of the concave mirror, and configured to acquire a first data set group in an A-scan direction by performing optical coherence tomography on a subject's eye placed at a subject's eye position or a conjugate position of the subject's eye position using light reflected by the reflective surface;
a storage unit including a memory and configured to store correction data for correcting an incident angle of the light at the subject's eye position depending on a deflection angle of the light by the optical scanner; and
a correction unit including processing circuitry configured to generate a second data set group by correcting at least a part of the first data set group based on the correction data stored in the storage unit, wherein the optical scanner includes:
a first scanner configured to deflect the light in a first deflection direction; and
a second scanner configured to deflect the light in a second deflection direction toward the subject's eye, the light being deflected by the first scanner, and
the processing circuitry in the correction unit is further configured to be capable of switching one of correction processing for at least a part of the first data set group based on first correction data for correcting the incident angle depending on the deflection angle of the light deflected by the first scanner and correction processing for at least a part of the first data set group based on second correction data for correcting the incident angle depending on the deflection angle of the light deflected by the second scanner, and of performing the switched correction processing.

9. The ophthalmologic apparatus of claim 1, wherein
the storage unit is configured to store a plurality of correction data corresponding to a plurality of scan conditions in which at least one of a deflection angle range and a deflection speed of the optical scanner is different, and
the processing circuitry in the correction unit is configured to correct at least a part of the first data set group based on the correction data stored in the storage unit corresponding to the scan condition.

10. The ophthalmologic apparatus of claim 1, wherein the processing circuitry is further configured as an image forming unit configured to form a tomographic image of the subject's eye based on the second data set group generated by the correction unit.

11. A method of controlling an ophthalmologic apparatus including a concave mirror and an optical scanner configured to deflect light from a light source to guide to a reflective surface of the concave mirror, the method comprising:
a data acquisition step of acquiring a first data set group in an A-scan direction by performing optical coherence tomography on a subject's eye placed at a subject's eye position or a conjugate position of the subject's eye position using light reflected by the reflective surface; and
a correction step of generating a second data set group by correcting at least a part of the first data set group based on correction data for correcting an incident angle of the light at the subject's eye position depending on a deflection angle of the light by the optical scanner, wherein
the correction step includes correcting one or more data sets corresponding to at least a part of a range of the incident angle in the first data set group so that the first data set group is a data set group acquired based on light incident at substantially equal intervals at the subject's eye position.

12. The method of controlling the ophthalmologic apparatus of claim 11, wherein
the concave mirror is an ellipsoidal mirror,
the optical scanner is disposed at a first focal point of the ellipsoidal mirror, near the first focal point, a conjugate position of the first focal point, or near the conjugate position, and the subject's eye position is disposed at a second focal point of the ellipsoidal mirror, near the second focal point, a conjugate position of the second focal point, or near the conjugate position of the second focal point.

13. A method of controlling an ophthalmologic apparatus including a concave mirror and an optical scanner configured to deflect light from a light source to guide to a reflective surface of the concave mirror, the method comprising:
a data acquisition step of acquiring a first data set group in an A-scan direction by performing optical coherence tomography on a subject's eye placed at a subject's eye position or a conjugate position of the subject's eye position using light reflected by the reflective surface; and
a correction step of generating a second data set group by correcting at least a part of the first data set group based on correction data for correcting an incident angle of the light at the subject's eye position depending on a deflection angle of the light by the optical scanner, wherein
the optical scanner includes:
a first scanner configured to deflect the light in a first deflection direction; and
a second scanner configured to deflect the light in a second deflection direction toward the subject's eye, the light being deflected by the first scanner, and
the correction step is capable of switching one of correction processing for at least a part of the first data set group based on first correction data for correcting the incident angle depending on the deflection angle of the light deflected by the first scanner and correction processing for at least a part of the first data set group based on second correction data for correcting the incident angle depending on the deflection angle of the light deflected by the second scanner, and of performing the switched correction processing.

14. The method of controlling the ophthalmologic apparatus of claim 11, further comprising
an image forming step of forming a tomographic image of the subject's eye based on the second data set group generated in the correction step.

15. The ophthalmologic apparatus of claim 8, wherein
the storage unit is configured to store a plurality of correction data corresponding to a plurality of scan conditions in which at least one of a deflection angle range and a deflection speed of the optical scanner is different, and
the processing circuitry in the correction unit is configured to correct at least a part of the first data set group based on the correction data stored in the storage unit corresponding to the scan condition.

16. The ophthalmologic apparatus of claim 8, wherein the processing circuitry is further configured as an image forming unit configured to form a tomographic image of the subject's eye based on the second data set group generated by the correction unit.

17. The method of controlling the ophthalmologic apparatus of claim 13, further comprising
an image forming step of forming a tomographic image of the subject's eye based on the second data set group generated in the correction step.

* * * * *